US010874322B2

(12) United States Patent
Gill et al.

(10) Patent No.: US 10,874,322 B2
(45) Date of Patent: Dec. 29, 2020

(54) METHOD AND SYSTEM TO DETECT PREMATURE VENTRICULAR CONTRACTIONS IN CARDIAC ACTIVITY SIGNALS

(71) Applicant: PACESETTER, INC., Sylmar, CA (US)

(72) Inventors: Jong Gill, Valencia, CA (US); Fujian Qu, San Jose, CA (US); Neha Malhotra, Los Angeles, CA (US); Stuart Rosenberg, Castaic, CA (US); Gene A. Bornzin, Simi Valley, CA (US); Fady Dawoud, Santa Monica, CA (US)

(73) Assignee: PACESETTER, INC., Sylmar, CA (US)

( * ) Notice: Subject to any disclaimer, the term of this patent is extended or adjusted under 35 U.S.C. 154(b) by 236 days.

(21) Appl. No.: 15/973,307

(22) Filed: May 7, 2018

(65) Prior Publication Data
US 2019/0336032 A1    Nov. 7, 2019

(51) Int. Cl.
*A61B 5/0452* (2006.01)
*A61B 5/024* (2006.01)
*A61B 5/0472* (2006.01)
*A61B 5/046* (2006.01)

(52) U.S. Cl.
CPC ...... *A61B 5/04525* (2013.01); *A61B 5/02405* (2013.01); *A61B 5/0472* (2013.01); *A61B 5/046* (2013.01)

(58) Field of Classification Search
CPC .......................... A61B 5/04525; A61B 5/02405
USPC ........................................................ 600/516
See application file for complete search history.

(56) References Cited

U.S. PATENT DOCUMENTS

| | | | |
|---|---|---|---|
| 3,946,744 | A | 3/1976 | Auerbach |
| 5,713,367 | A | 2/1998 | Arnold et al. |
| 7,248,921 | B2 | 7/2007 | Palreddy et al. |
| 7,294,108 | B1 | 11/2007 | Bornzin et al. |
| 7,894,894 | B2 | 2/2011 | Stadler et al. |
| 8,135,456 | B2 | 3/2012 | Haluska |
| 8,260,404 | B1 | 9/2012 | Bharmi et al. |
| 8,332,022 | B2 | 12/2012 | Brown et al. |

(Continued)

OTHER PUBLICATIONS

Extended Search Report, dated Jul. 15, 2019—Counterpart EP Pat Appl No. 19172673.6.

(Continued)

*Primary Examiner* — Nadia A Mahmood
(74) *Attorney, Agent, or Firm* — The Small Patent Law Group LLC; Dean D. Small

(57) ABSTRACT

A computer implemented method and system are provided for detecting premature ventricular contractions (PVCs) in cardiac activity. The method and system obtain cardiac activity (CA) signals for a series of beats, and, for at least a portion of the series of beats, calculate QRS scores for corresponding QRS complex segments from the CA signals. The method and system calculate a variability metric for QRS scores across the series of beats, calculate a QRS complex template using QRS segments from the series of beats, calculate correlation coefficients between the QRS complex template and the QRS complex segments, compare the variability metric to a variability threshold and the correlation coefficients to a correlation threshold, and designate the CA signals to include a predetermined level of PVC burden based on the comparing.

21 Claims, 12 Drawing Sheets

(56) References Cited

U.S. PATENT DOCUMENTS

| | | |
|---|---|---|
| 8,391,980 B2 | 3/2013 | Bornzin et al. |
| 8,831,713 B2 | 9/2014 | Stadler et al. |
| 8,831,747 B1 | 9/2014 | Min et al. |
| 9,044,610 B2 | 6/2015 | Rosenberg et al. |
| 9,174,062 B2 | 11/2015 | Stadler et al. |
| 9,216,285 B1 | 12/2015 | Boling et al. |
| 9,232,485 B2 | 1/2016 | Wu et al. |
| 9,333,351 B2 | 5/2016 | Arnold et al. |
| 9,486,155 B2 | 11/2016 | Sarkar et al. |
| 2006/0235476 A1 | 10/2006 | Gunderson et al. |
| 2008/0082014 A1 | 4/2008 | Cao et al. |
| 2009/0270749 A1 | 10/2009 | Haluska |
| 2009/0281587 A1 | 11/2009 | Pei |
| 2012/0029373 A1 | 2/2012 | Stadler et al. |
| 2013/0138005 A1 | 5/2013 | Dong et al. |
| 2015/0038863 A1 | 2/2015 | Schotten et al. |
| 2016/0213270 A1 | 7/2016 | Cao et al. |
| 2017/0251940 A1 | 9/2017 | Perschbacher et al. |
| 2017/0273589 A1 | 9/2017 | Sarkar et al. |
| 2018/0064360 A1 | 3/2018 | Siejko et al. |

OTHER PUBLICATIONS

Extended European Search Report for corresponding EP Application No. 19172674.4 dated Oct. 4, 2019 (8 pages).
Extended European Search Report for corresponding EP Application No. 19172673.6 dated Jul. 15, 2019 (5 pages).

147

Reason for Monitoring:        Implant Date:
Cryptogenic Stroke            3 MAR 2018

Last Clinic Session:   14 AUG 2018    Remaining Battery    R-Wave Amplitude
Last Remote Session: N/A              Capacity             0.46 mV (3 AUG 2018 21:55)
Last Read:             Today (3:15)
Last Cleared:          14 AUG 2018

Presenting Rhythm         Sweep Speed: 12.3 mm/s

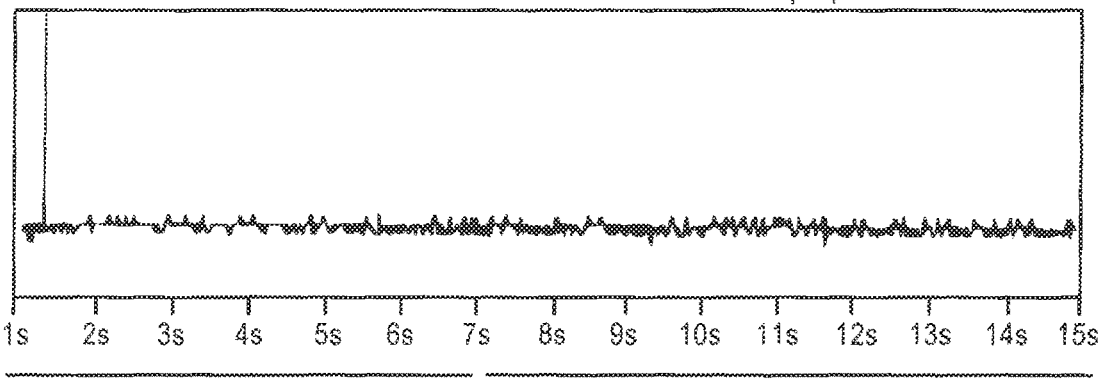

1s  2s  3s  4s  5s  6s  7s  8s  9s  10s  11s  12s  13s  14s  15s

Episode Counts: Since 14AUG 2018

| | |
|---|---|
| AF | 10 |
| Tachy | 0 |
| Brady | 0 |
| Pause | 1 |
| Symptom (all) | 0 |
| Symptom (with Detection) | 0 |

Key Parameters

| | | |
|---|---|---|
| AF Episode | ✓ | 2 min |
| Tachy Episode | ✓ | 250 bpm, 50 intervals |
| | ✓ | |
| Brady Episode | ✓ | 30 bpm |
| Pause Episode | ✓ | 5.0 sec |
| Patient Activated Episode | | |
| EGM Dynamic Range | | ± 0.80 mV |
| Max Sensitivity | | 0.1 mv |

Ventricular Heart Rate Histogram Since 14 Aug 2018

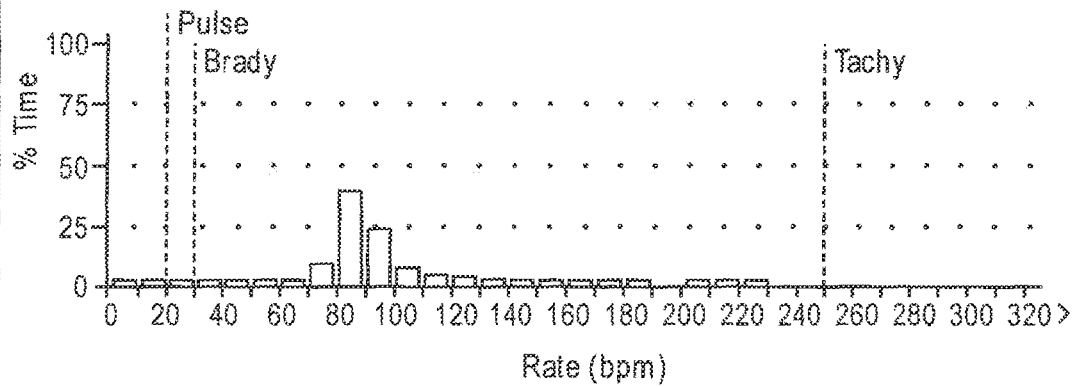

FIG. 2D

METHOD AND SYSTEM TO DETECT PREMATURE VENTRICULAR CONTRACTIONS IN CARDIAC ACTIVITY SIGNALS

RELATED APPLICATIONS

The following applications relate to and are filed concurrently on the same day as the present application, and are expressly incorporated herein by reference in their entireties (hereafter referred to as "Related Applications"):

U.S. patent application Ser. No. 15/973,126, titled "METHOD AND SYSTEM FOR SECOND PASS CONFIRMATION OF DETECTED CARDIAC ARRHYTHMIC PATTERNS" published as U.S. 2019/0336025, U.S. patent application Ser. No. 15/973,107, titled "METHOD AND SYSTEM TO DETECT P-WAVES IN CARDIAC ARRHYTHMIC PATTERNS" published as U.S. 2019/0336031, U.S. patent application Ser. No. 15/973,351, titled "METHOD AND SYSTEM TO DETECT R-WAVES IN CARDIAC ARRHYTHMIC PATTERNS" published as U.S. 2019/0336026, and U.S. patent application Ser. No. 15/973,384, titled "METHOD AND SYSTEM TO DETECT NOISE IN CARDIAC ARRHYTHMIC PATTERNS" published as U.S. 20190336083.

FIELD OF THE INVENTION

Embodiments herein relate generally to implantable medical devices, and more particularly to detection and discrimination of underlying arrhythmic events based on presence of post ventricular contractions (PVCs).

BACKGROUND OF THE INVENTION

Today, numerous atrial fibrillation (AF) detection processes are implemented within implantable cardiac monitors (ICMs) that detect atrial fibrillation based on irregularities and variation patterns in R-wave to R-wave (RR) intervals. In some embodiments, the AF detection process steps beat by beat through cardiac activity (CA) signals and analyzes the RR intervals over a period of time. An AF episode is declared when the RR interval pattern for the suspect beat segments is sufficiently irregular and dissimilar from RR interval patterns for sinus beat segments.

However, AF detection processes may declare false AF episodes where the ICM provides a device documented AF episode, even though a patient is not experiencing AF. False AF detection may arise due to various conditions and behavior of the heart, such as when a patient experiences sick sinus rhythms with irregular RR intervals, experiences frequent premature ventricular contractions (PVCs) and/or inappropriate R-wave sensing. To an extent, false AF detection is due, in part, to dependence of the AF detection process upon identification of R-wave features, with little or no input concerning other features of a cardiac event. PVCs, in general, introduce unstable RR intervals, such as short-long RR intervals, where the instability may give rise to erroneous declaration of an AF episode. Thus, PVCs present a substantial challenge in connection with AF detection algorithms that rely on RR interval variability.

SUMMARY

In accordance with embodiments herein, a computer implemented method is provided for detecting premature ventricular contractions (PVCs) in cardiac activity. The method is under control of one or more processors configured with specific executable instructions. The method obtains cardiac activity (CA) signals for a series of beats. For at least a portion of the series of beats, the method calculates QRS scores for corresponding QRS complex segments from the CA signals. The method calculates a variability metric for QRS scores across the series of beats, a QRS complex template using QRS segments from the series of beats and a correlation coefficients between the QRS complex template and the QRS complex segments. the method compares the variability metric to a variability threshold and the correlation coefficients to a correlation threshold and designates the CA signals to include a predetermined level of PVC burden based on the comparing.

Optionally, the calculating the QRS scores may comprise calculating at least one of a summation, area under a curve, or energy for the QRS complex segments. The method may further comprise creating a morphology ensemble from the QRS complex segments and may compare the morphology ensemble to QRS morphologies for the corresponding QRS complex segments to obtain morphology correlation characteristics for the QRS complex segments. The computing of the variability metric may include calculating a covariance Cov_QRS from the QRS scores. The covariance may be based on the QRS scores. The covariance Cov_QRS may represent a standard deviation of the QRS scores of the QRS complex segments divided by an average of the QRS scores. The QRS scores may represent at least one of amplitude sums, energy or area under the curve for the corresponding QRS complex segments.

Optionally, the variability metric may not satisfy the variability threshold, and may declare the CA signals to include an non-significant PVC burden which is less than the predetermined level of PVC burden. The morphology ensemble may represent an ensemble average of the QRS morphologies for a desired number of the QRS complex segments. The comparing may include comparing the QRS morphologies for the corresponding QRS complex segments to the ensemble average to obtain the morphology correlation characteristics. The morphology correlation characteristics may represent correlations between the ensemble average and the QRS morphologies of each of the QRS complex segments. The method may further comprise rejecting the beats from the CA signals that exhibit a predetermined level of baseline drift. The variability metric may satisfy the variability threshold and the correlation coefficients may satisfy the correlation conditions, declaring the CA signals to have significant PVC burden.

In accordance with embodiments herein, a system is provided for detecting premature ventricular contractions (PVCs) in cardiac activity. The system comprises memory to store executable instructions. One or more processors that, when executing the executable instructions, are configured to: obtain a cardiac activity (CA) signals for a series of beats. For at least a portion of the series of beats, the system calculates QRS scores for corresponding QRS complex segments from the CA signals. The system calculates a variability metric for QRS scores across the series of beats, calculates a QRS complex template using the QRS complex segments and calculates correlation coefficients between the QRS complex template and the QRS complex segment. The system compares the variability metric to a variability threshold and the correlation coefficients to a correlation threshold and designates the CA signals to include a predetermined level of PVC burden based on the comparing.

Optionally, the one or more processors are configured to calculate the QRS scores comprises calculating at least one of a summation, area under a curve, or energy for the QRS complex segments. The one or more processors may be configured to create a morphology ensemble from the QRS complex segments and may compare the morphology ensemble to QRS morphologies for the corresponding QRS complex segments to obtain morphology correlation characteristics for the QRS complex segments. The designation may be based on the morphology correlation characteristics. The morphology correlation characteristic may represent an average correlation coefficient. The determining may include determining whether the average correlation coefficient is smaller than the predetermined threshold. The morphology correlation characteristic may represent a minimum correlation coefficient. The determining may include determining whether the minimum correlation coefficient for the QRS complex segments is smaller than a minimum threshold.

Optionally, the morphology ensemble may represent an ensemble average of the QRS morphologies for a desired number of the QRS complex segments. The comparing may include comparing the QRS morphologies for the corresponding QRS complex segments to the ensemble average to obtain the morphology correlation characteristics. The one or more processors may be configured to compute the variability metric by calculating a covariance $Cov\_QRS_{SUM}$ from the QRS scores, the covariance based on the QRS complex segments. The variability metric may not satisfy the variability threshold, the system may declare the CA signals to include non-significant PVC burden which is less than the predetermined level of PVC burden. The correlation coefficients may not satisfy the correlation threshold. The system may declare the CA signals do not have significant PVC burden. The variability metric may be satisfied the variability threshold and the correlation coefficients satisfy the correlation threshold, declaring the CA signals to have significant PVC burden. When declaring the CA signals to have significant PVC burden, the system may reject an original detection of AF episode, or reevaluating if the CA signals include AF by excluding identified PVC beats.

In accordance with embodiments herein, methods and devices are provided for determining if a CA signal contains a significant number of PVC beats. Embodiments herein utilize an aspect that PVC beats exhibit different morphology in the QRS segment compared to non-PVC beats conducted from atria. Embodiments herein provide a PVC detection method and device that is configured to operate in aggregate on a device signal segments (e.g., EGM strip of determined length). The PVC detection methods and devices may be performed in real time by an IMD while the IMD is sensing CA activity and/or in connection with post processing in non-real time applications. The PVC methods and devices herein avoid a need to compare each beat to a predefined sinus template, as performed by traditional PVC discrimination algorithms.

The methods and devices described herein may be implemented as a "first pass" process to rapidly identify whether an EGM strip or arrhythmia episode includes a predetermined level (e.g., high) of PVC burden that may otherwise call into question a prior diagnosis (e.g., a determination by an IMD that the CA signals exhibit an arrhythmia episode such as AF). Additionally, or alternatively, at least some embodiments may provide an adaptive template generation process in which morphology templates are generated "on-the-fly" during operation based on a history of CA signals exhibited by the individual patient. The automatically generated templates may then be utilized to identify specific beats within an episode that represent PVC events. The beats that represent PVC events may then be flagged to be excluded from further processing in connection with analyzing a series of CA signals for an arrhythmia.

In accordance with embodiments herein, methods and devices are described that may be implemented as a "second pass" or "confirmation pass" to analyze device documented episodes. In a second pass implementation, the methods and devices herein re-analyze the CA signals previously analyzed by the IMD to determine whether the arrhythmia detection made by the IMD is true or false. PVCs tend to introduce a short RR interval followed by long RR interval. The presence of frequent PVC beats may lead the IMD to identify sufficient irregularities in the RR intervals which in turn leads the IMD to declare are AF episode. The methods and devices herein allow identification of high PVC burden in the CA signal and reject false detection initially declared by the IMD.

BRIEF DESCRIPTION OF THE DRAWINGS

FIG. 2D illustrates screenshots of displays in which episode statistics and arrhythmia diagnostics may be presented to a physician in accordance with an embodiment herein.

I. TERMS AND ABBREVIATIONS

Figure 1:
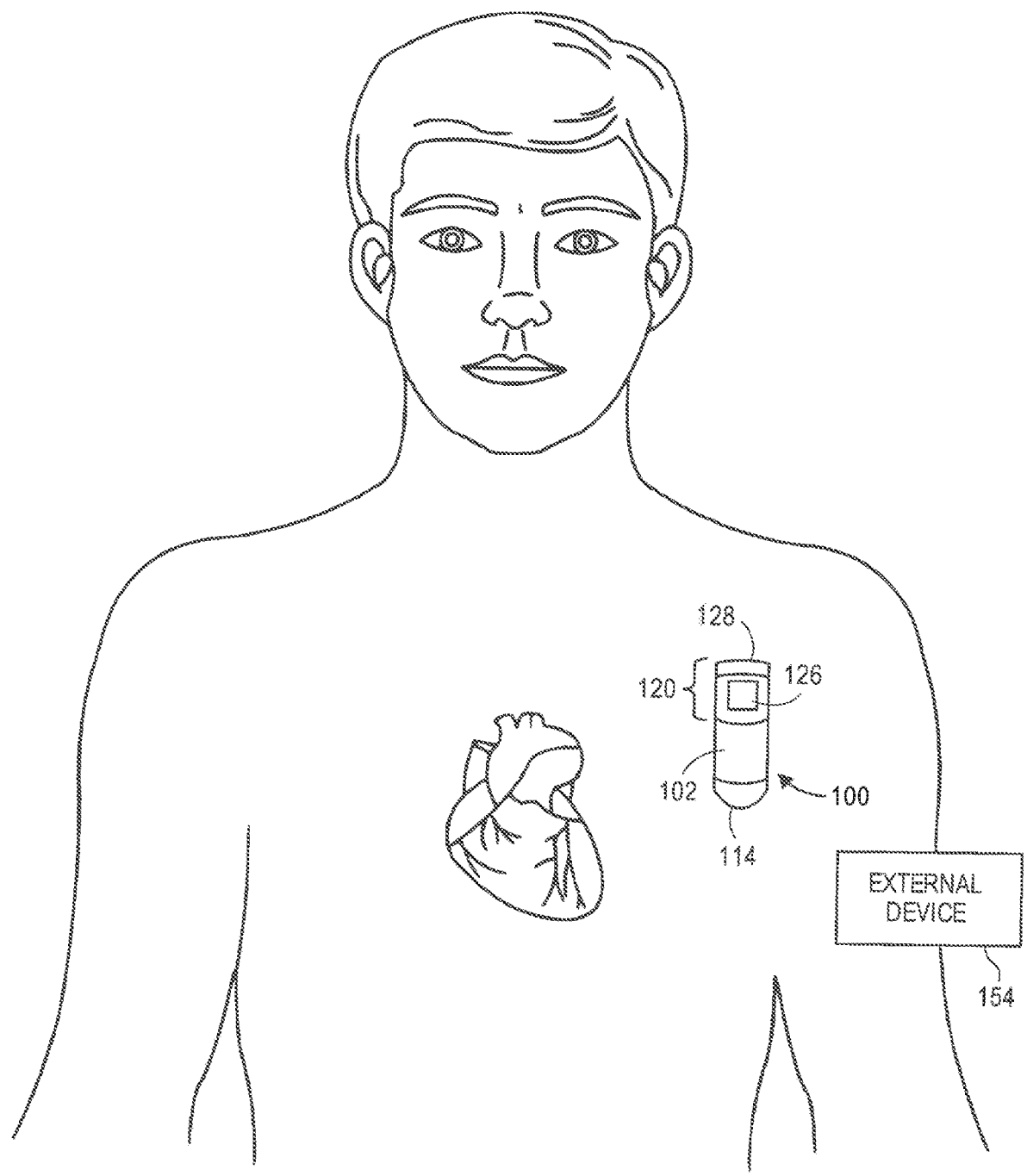
FIG. 1 illustrates an implantable cardiac monitoring device (ICM) intended for subcutaneous implantation at a site near the heart in accordance with embodiments herein.

The terms "cardiac activity signal", "cardiac activity signals", "CA signal" and "CA signals" (collectively "CA signals") are used interchangeably throughout to refer to an analog or digital electrical signal recorded by two or more electrodes positioned subcutaneous or cutaneous, where the electrical signals are indicative of cardiac electrical activity. The cardiac activity may be normal/healthy or abnormal/ arrhythmic. Nonlimiting examples of CA signals include ECG signals collected by cutaneous electrodes, and EGM signals collected by subcutaneous electrodes.

The terms "cardiac activity data set" and "CA data set" (collectively "CA data set") are used interchangeably to refer to a data set that includes measured CA signals for a series of cardiac events in combination with device documented markers.

The term "marker" refers to data and/or information identified from CA signals that may be presented as graphical and/or numeric indicia indicative of one or more features within the CA signals and/or indicative of one or more episodes exhibited by the cardiac events. Markers may be superimposed upon CA signals or presented proximate to, and temporally aligned with, CA signals. Non-limiting examples of markers may include R-wave markers, noise markers, activity markers, interval markers, refractory markers, P-wave markers, T-wave markers, PVC markers, sinus rhythm markers, AF markers and other arrhythmia markers. As a further nonlimiting example, basic event markers may include "AF entry" to indicate a beginning of an AF event, "in AF" to indicate that AF is ongoing, "AF exit" to indicate that AF has terminated, "T" to indicate a tachycardia beat, "B" to indicate a bradycardia beat, "A" to indicate an asystole beat, "VS" to indicate a regular sinus beat, "Tachy" to indicate a tachycardia episode, "Brady" to indicate a Bradycardia episode, "Asystole" to indicate an asystole episode, "Patient activated" to indicate a patient activated episode. An activity marker may indicate activity detected by activity sensor during the CA signal. Noise markers may indicate entry/start, ongoing, recovery and exit/stop of noise. Markers may be presented as symbols, dashed lines, numeric values, thickened portions of a waveform, and the like. Markers may represent events, intervals, refractory periods, ICM activity, and other algorithm related activity. For example, interval markers, such as the R-R interval, may include a numeric value indicating the duration of the interval. The AF markers indicate atrial fibrillation rhythmic.

The term "device documented marker" refers to markers that are declared by an implantable cardiac monitor and/or implantable medical device. Any or all of the foregoing examples of markers represent device document markers. Markers may be declared based on numerous criteria, such as signal processing, feature detection and AF detection software and hardware within and/or operating on the implantable cardiac monitor and/or implantable medical device.

The term "FOI" refers to a feature of interest within CA signals. Nonlimiting examples of features of interest include an R-wave, P-wave, T-wave and isoelectric segments. A feature of interest may correspond to a peak of an individual R-wave, an average or median P, R or T-wave peak and the like.

The terms "beat" and "cardiac event" are used interchangeably and refer to both normal or abnormal events.

The terms "normal" and "sinus" are used to refer to events, features, and characteristics of, or appropriate to, a heart's healthy or normal functioning.

The terms "abnormal," or "arrhythmic" are used to refer to events, features, and characteristics of, or appropriate to, a un-healthy or abnormal functioning of the heart.

The term "real-time" refers to a time frame contemporaneous with a normal or abnormal episode occurrences. For example, a real-time process or operation would occur during or immediately after (e.g., within minutes or seconds after) a cardiac event, a series of cardiac events, an arrhythmia episode, and the like.

The term "adaptive", as used in connection with a sensitivity profile, sensitivity limit, sensitivity level or other sensing parameters, refers to an ability of the processes herein to modify the value of sensitivity and/or sensing parameters based on features within the CA signals. The sensitivity profile parameters may include refractory period, start sensitivity, decay delay, sensitivity limit, slope of sensitivity decay, etc.

The term "sensitivity level", as used herein, refers to a threshold that an input CA signal must exceed for an implantable device to identify a QRS complex feature of interest (e.g., an R-wave). As one non-limiting example, software may be implemented using a programmed sensitivity level to declare an R-wave to be detected when the input CA signal exceeds the current programmed sensitivity level In response, the software declares a device documented feature (e.g., R-wave) marker. The sensitivity level may be defined in various manners based on the nature of the CA signals. For example, when the CA signals measure electrical activity in terms of millivolts, the sensitivity level represents a millivolt threshold. For example, when a cardiac beat with a 0.14 mV amplitude is sensed by a device hardware, and R-wave may be detected when the current sensitivity level is programmed to 0.1 mV. However, when the sensitivity level is programmed to 0.15 mV or above, a cardiac beat with an amplitude of 0.14 mV will not be detected as an R-wave. Embodiments herein determine an adaptive sensitivity limit and sensitivity profile for the sensitivity level.

The term "turn", as used herein to refer to characteristics of a shape or morphology of a CA signal, shall mean changes in a direction of the CA signal. For example, the CA signal may turn by changing direction from a signal having a positive slope to a negative slope, or from a signal having a negative slope to a positive slope. Turns may have various associated characteristics such as amplitude, frequency (e.g., number of turns per unit time) and duration (e.g., an amount of time for the signal to exceed and drop below a desired percentage of the signal peak).

The terms "significant" and "non-significant", when used in connection with describing PVC burden, refer to an amount of PVC burden that is, or is not, sufficient to cause an AF detection algorithm to declare a false arrhythmia episode. A small number of PVC events, and/or a collection of PVC events that are spaced substantially apart from one another over time, may not be sufficient to be considered "significant" as the PVC events do not cause the AF detection algorithm to declare a false arrhythmia episode. Alternatively, when a sufficient number of PVC events occur within a relatively short period of time, the potential exists that the AF detection algorithm incorrectly identifies R-waves within the PVC events, leading to a declaration of a false arrhythmia episode. For example, a 30-45 second strip of EGM signals may include one or more PVC events that cause the AF detection algorithm of an IMD to designate a false R-wave marker. Based on the number of false R-wave markers in the EGM strip, the AF detection algorithm may determine that no arrhythmia episode is present or a false arrhythmia episode is present.

II. SYSTEM OVERVIEW

FIG. 1 illustrates an implantable cardiac monitoring device (ICM) 100 intended for subcutaneous implantation at a site near the heart. The ICM 100 includes a pair of spaced-apart sense electrodes 114, 126 positioned with respect to a housing 102. The sense electrodes 114, 126 provide for detection of far field electrogram signals. Numerous configurations of electrode arrangements are possible. For example, the electrode 114 may be located on a distal end of the ICM 100, while the electrode 126 is located on a proximal side of the ICM 100. Additionally, or alternatively, electrodes 126 may be located on opposite sides of the ICM 100, opposite ends or elsewhere. The distal electrode 114 may be formed as part of the housing 102, for example, by coating all but a portion of the housing with a nonconductive material such that the uncoated portion forms the electrode 114. In this case, the electrode 126 may be electrically isolated from the housing 114 electrode by placing it on a component separate from the housing 102, such as the header 120. Optionally, the header 120 may be formed as an integral portion of the housing 102. The header 120 includes an antenna 128 and the electrode 126. The antenna 128 is configured to wirelessly communicate with an external device 154 in accordance with one or more predetermined wireless protocols (e.g., Bluetooth, Bluetooth low energy, Wi-Fi, etc.). The housing 102 includes various other components such as: sense electronics for receiving signals from the electrodes, a microprocessor for processing the signals in accordance with algorithms, such as the AF detection algorithm described herein, a loop memory for temporary storage of CA data, a device memory for long-term storage of CA data upon certain triggering events, such as AF detection, sensors for detecting patient activity and a battery for powering components.

In at least some embodiments, the ICM 100 is configured to be placed subcutaneously utilizing a minimally invasive approach. Subcutaneous electrodes are provided on the housing 102 to simplify the implant procedure and eliminate a need for a transvenous lead system. The sensing electrodes may be located on opposite sides of the device and designed to provide robust episode detection through consistent contact at a sensor—tissue interface. The ICM 100 may be configured to be activated by the patient or automatically activated, in connection with recording subcutaneous ECG signals.

The ICM 100 senses far field, subcutaneous CA signals, processes the CA signals to detect arrhythmias and if an arrhythmia is detected, automatically records the CA signals in memory for subsequent transmission to an external device 154. The CA signal processing and AF detection is provided for, at least in part, by algorithms embodied in or implemented by the microprocessor. The ICM 100 includes one or more processors and memory that stores program instructions directing the processors to implement AF detection utilizing an on-board R-R interval irregularity (ORI) process that analyzes cardiac activity signals collected over one or more sensing channels.

Figure 2A:
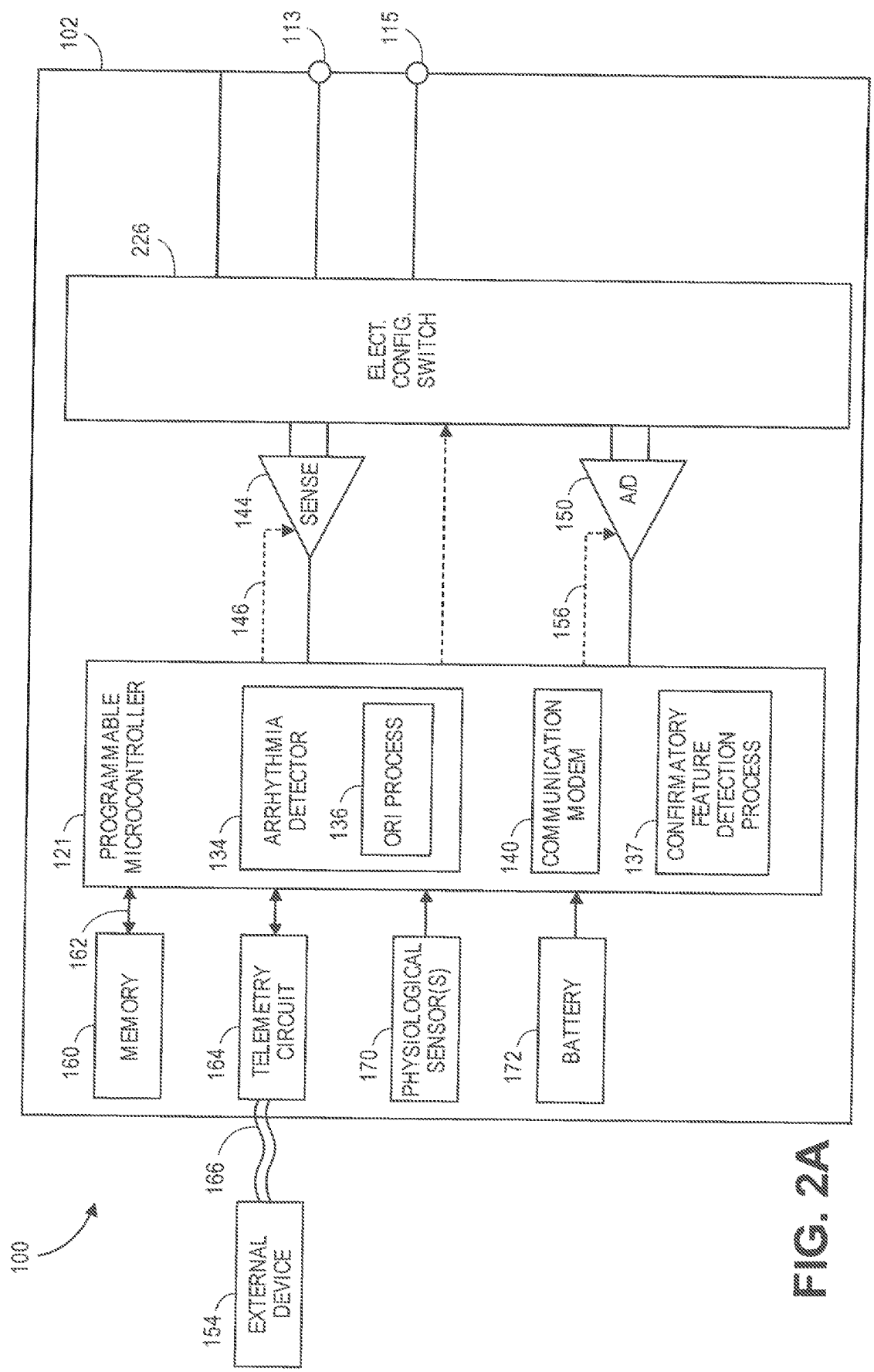
FIG. 2A shows a block diagram of the ICM formed in accordance with embodiments herein.

FIG. 2A shows a block diagram of the ICM 100 formed in accordance with embodiments herein. The ICM 100 may be implemented to monitor ventricular activity alone, or both ventricular and atrial activity through sensing circuitry. The ICM 100 has a housing 102 to hold the electronic/computing components. The housing 102 (which is often referred to as the "can", "case", "encasing", or "case electrode") may be programmably selected to act as an electrode for certain sensing modes. Housing 102 further includes a connector (not shown) with at least one terminal 113 and optionally additional terminals 115. The terminals 113, 115 may be coupled to sensing electrodes that are provided upon or immediately adjacent the housing 102. Optionally, more than two terminals 113, 115 may be provided in order to support more than two sensing electrodes, such as for a bipolar sensing scheme that uses the housing 102 as a reference electrode. Additionally, or alternatively, the terminals 113, 115 may be connected to one or more leads having one or more electrodes provided thereon, where the electrodes are located in various locations about the heart. The type and location of each electrode may vary.

The ICM 100 includes a programmable microcontroller 121 that controls various operations of the ICM 100, including cardiac monitoring. Microcontroller 121 includes a microprocessor (or equivalent control circuitry), RAM and/or ROM memory, logic and timing circuitry, state machine circuitry, and I/O circuitry. The microcontroller 121 also performs the operations described herein in connection with collecting cardiac activity data and analyzing the cardiac activity data to identify AF episodes.

A switch 127 is optionally provided to allow selection of different electrode configurations under the control of the microcontroller 121. The electrode configuration switch 127 may include multiple switches for connecting the desired electrodes to the appropriate I/O circuits, thereby facilitating electrode programmability. The switch 127 is controlled by a control signal 128 from the microcontroller 121. Optionally, the switch 127 may be omitted and the I/O circuits directly connected to the housing electrode 114 and a second electrode 126. Microcontroller 121 includes an arrhythmia detector 134 that is configured to analyze cardiac activity signals to identify potential AF episodes as well as other arrhythmias (e.g., Tachycardias, Bradycardias, Asystole, etc.). By way of example, the arrhythmia detector 134 may implement an AF detection algorithm as described in U.S. Pat. No. 8,135,456, the complete subject matter of which is incorporated herein by reference. Although not shown, the microcontroller 121 may further include other dedicated circuitry and/or firmware/software components that assist in monitoring various conditions of the patient's heart and managing pacing therapies.

The ICM 100 is further equipped with a communication modem (modulator/demodulator) 140 to enable wireless communication. In one implementation, the communication modem 140 uses high frequency modulation, for example using RF, Bluetooth or Bluetooth Low Energy telemetry protocols. The signals are transmitted in a high frequency range and will travel through the body tissue in fluids without stimulating the heart or being felt by the patient. The communication modem 140 may be implemented in hardware as part of the microcontroller 121, or as software/firmware instructions programmed into and executed by the microcontroller 121. Alternatively, the modem 140 may reside separately from the microcontroller as a standalone component. The modem 140 facilitates data retrieval from a remote monitoring network. The modem 140 enables timely and accurate data transfer directly from the patient to an electronic device utilized by a physician.

The ICM 100 includes sensing circuitry 144 selectively coupled to one or more electrodes that perform sensing operations, through the switch 127 to detect cardiac activity data indicative of cardiac activity. The sensing circuitry 144 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the features of interest. In one embodiment, switch 127 may be used to determine the sensing polarity of the cardiac signal by selectively closing the appropriate switches.

The output of the sensing circuitry 144 is connected to the microcontroller 121 which, in turn, determines when to store the cardiac activity data of CA signals (digitized by the A/D data acquisition system 150) in the memory 160. For example, the microcontroller 121 may only store the cardiac activity data (from the A/D data acquisition system 150) in the memory 160 when a potential AF episode is detected. The sensing circuitry 144 receives a control signal 146 from the microcontroller 121 for purposes of controlling the gain, threshold, polarization charge removal circuitry (not shown), and the timing of any blocking circuitry (not shown) coupled to the inputs of the sensing circuitry.

In the example of FIG. 2A, a single sensing circuit 144 is illustrated. Optionally, the ICM 100 may include multiple sensing circuits, similar to sensing circuit 144, where each sensing circuit is coupled to two or more electrodes and controlled by the microcontroller 121 to sense electrical activity detected at the corresponding two or more electrodes. The sensing circuit 144 may operate in a unipolar sensing configuration or in a bipolar sensing configuration. Optionally, the sensing circuit 144 may be removed entirely and the microcontroller 121 perform the operations described herein based upon the CA signals from the A/D data acquisition system 150 directly coupled to the electrodes.

The arrhythmia detector 134 of the microcontroller 121 includes an on-board R-R interval irregularity (ORI) process 136 that detects AF episodes using an automatic detection algorithm that monitors for irregular ventricular rhythms that are commonly known to occur during AF. The ORI process 136 may be implemented as firmware, software and/or circuits. The ORI process 136 uses a hidden Markov Chains and Euclidian distance calculations of similarity to assess the transitionary behavior of one R-wave (RR) interval to another and compare the patient's RR interval transitions to the known RR interval transitions during AF and non-AF episodes obtained from the same patient and/or many patients. The ORI process 136 detects AF episodes over a short number of RR intervals. For example, the ORI process 136 may implement the AF detection methods described in U.S. Pat. No. 8,135,456, the complete subject matter of which is incorporated herein by reference in its entirety. As explained herein, the ORI process 136 manages a sensitivity profile of the sensor 144 during R-wave detection utilizing an automatic sensing control (ASC) adjustment to determine whether the CA signal has sufficient amplitude to be analyzed for cardiac events. The ORI process 136 identifies R-waves within the CA signals at points where the CA signal crosses the sensitivity profile (outside of a refractory period). The ORI process 136 tracks RR intervals within the CA signal and identifies AF events within the CA signal based on irregularities in the RR interval. When a sufficient number (e.g., X cardiac events out of Y cardiac events) of the cardiac events within the CA signal are identified as AF events, the ORI process 136 declares an AF episode.

Figure 3:
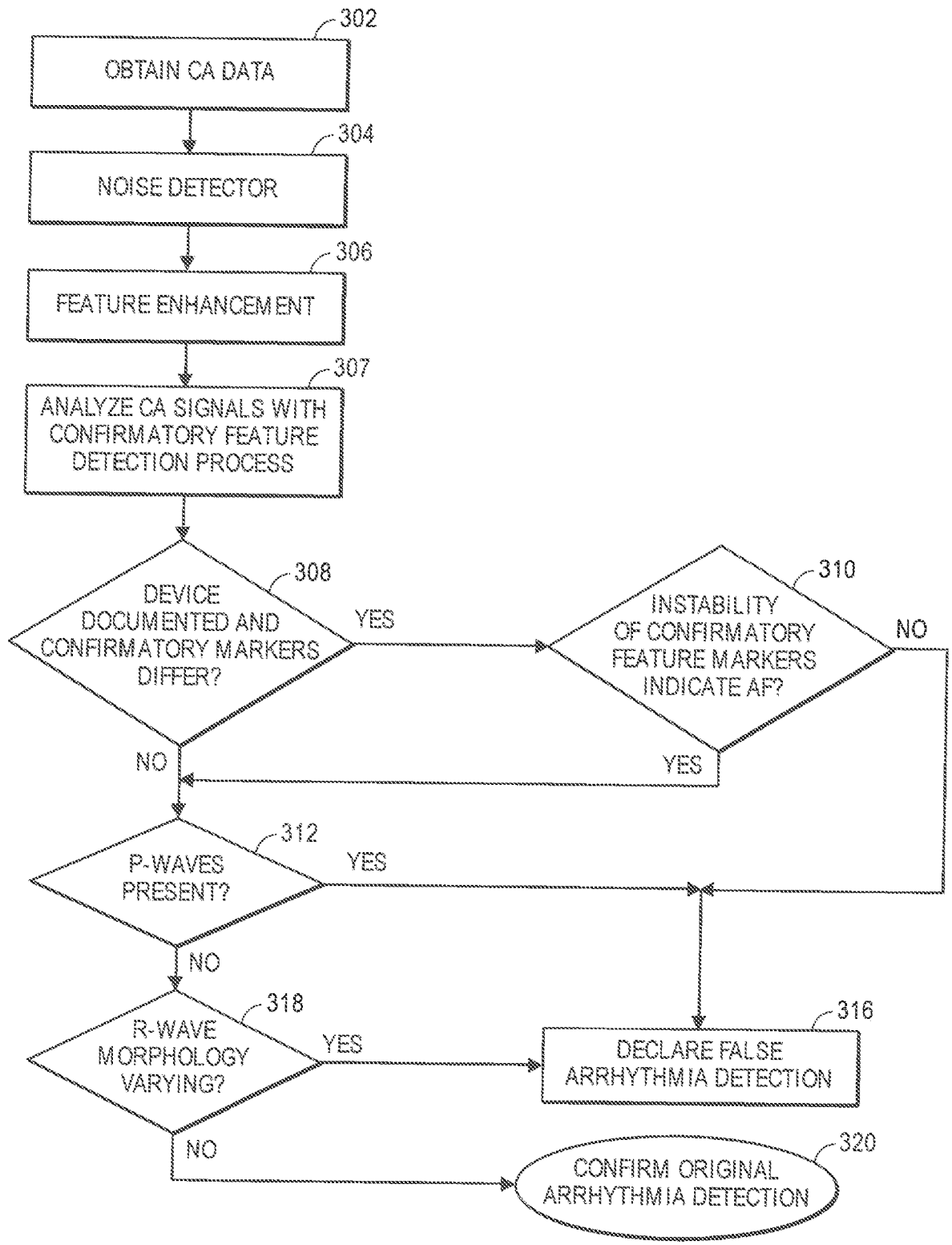
FIG. 3 shows a high-level workflow for an enhanced confirmatory AF detection process implemented in accordance with embodiments herein.
Figure 4:
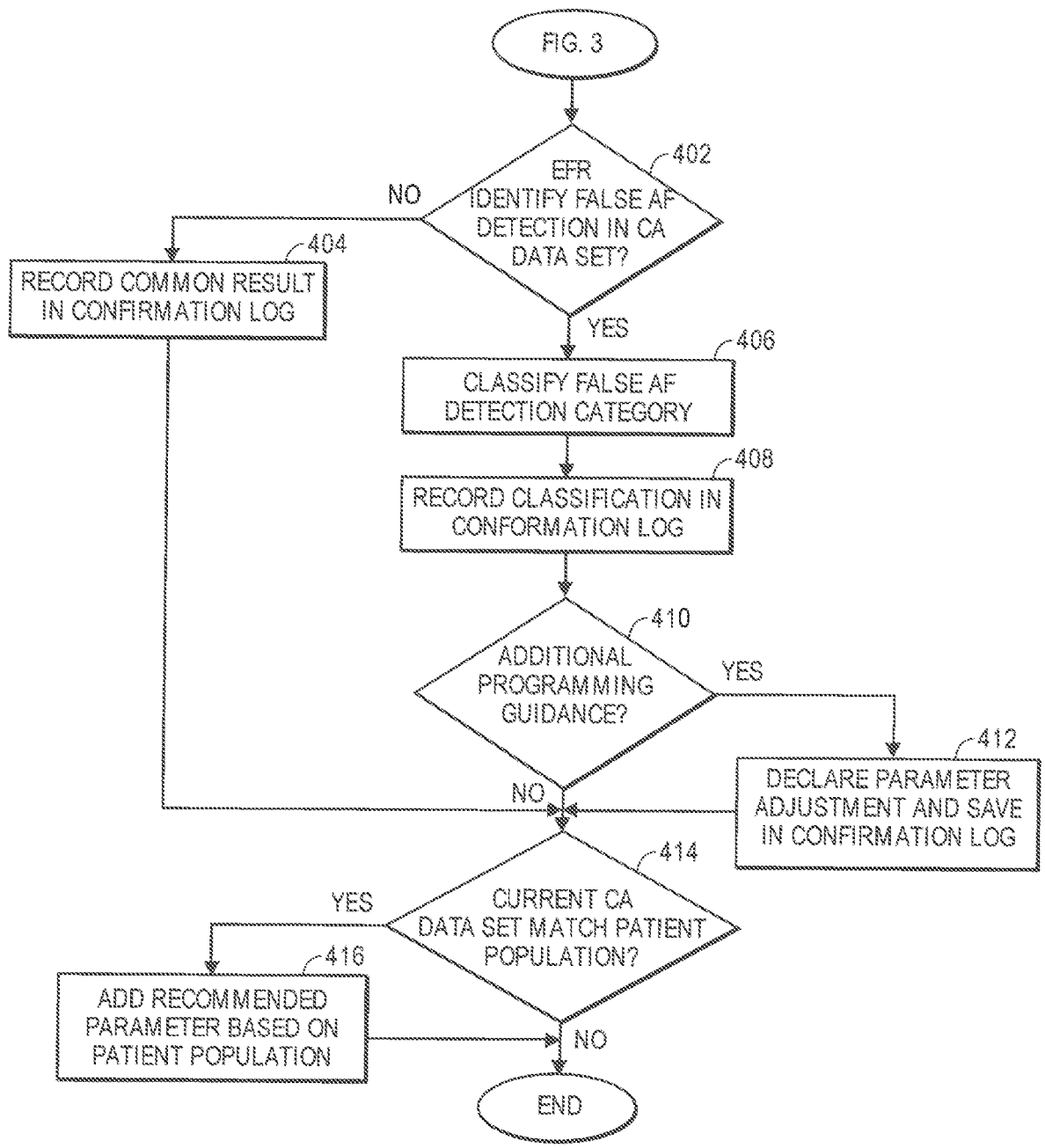
FIG. 4 illustrates a flow chart for classifying AF detection and developing recommendations for sensitivity profile parameter settings in accordance with embodiments herein.

Optionally, the microcontroller 121 may also include a confirmatory feature detection process 137 configured to implement one or more of the operations discussed herein, such as all or a portion of the enhanced confirmatory AF detection process of FIG. 3 and/or all or a portion of the AF detection classifying and recommendation process of FIG. 4. As a further example, the confirmatory feature detection process 137 may implement one or more of the R-wave detection processes, noise detection processes, P-wave detection processes and PVC detection processes described in the Co-Pending Related Applications.

Figure 2B:
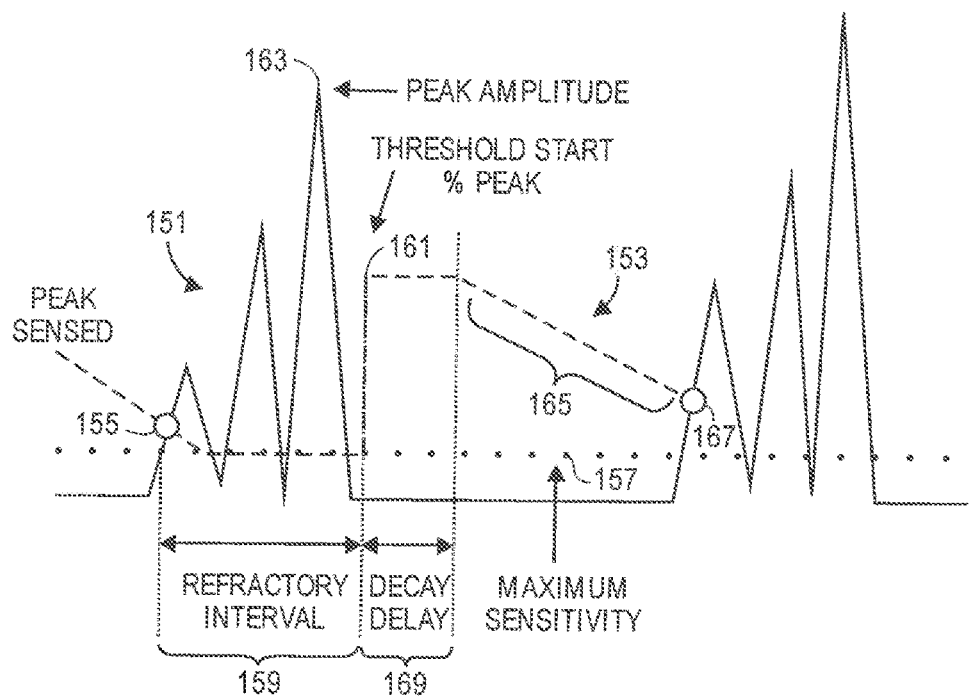
FIG. 2B illustrates an automatic sensing control adjustment utilized by the ORI process of the ICM in accordance with embodiments herein.

FIG. 2B illustrates an automatic sensing control adjustment utilized by the ORI process 136 of the ICM 100 in accordance with embodiments herein. FIG. 2B illustrates an example cardiac activity signal 151 after passing through a rectifier to convert all positive and negative deflections within the cardiac activity signal 151 to be positive deflections. The ORI process 136 manages the sensor 144 to have a sensitivity profile 163 (denoted by a dashed line) that varies over time.

In a basic implementation, the ORI process 136 utilizes a conventional automatic sensing control adjustment based on a conventional sensitivity profile 153. The sensitivity profile 153 is defined by sensitivity profile parameter settings corresponding to the threshold start sensitivity 161, decay delay time interval 169, maximum sensitivity 157 and slope of the sensitivity decay 165. Optionally, the sensitivity decay 165 may be defined in accordance with a non-linear monotonically changing shape from the threshold start sensitivity 161 to the maximum sensitivity 157. The start sensitivity parameter defines a start sensitivity of the sensitivity profile. For example, the start sensitivity parameter may set a start sensitivity to a percentage of the preceding R-wave peak amplitude. The refractory period/interval duration parameter defines a blanking interval beginning at a sensed R-wave, during which the processors do not search for a T-wave. The decay delay parameter defines the interval at which the sensitivity profile maintains the sensitivity level at a constant level following expiration of the refractory period before the sensitivity profile begins decreasing. When the sensitivity profile includes a linear sensitivity level decline, the decay delay rate defines a slope of the linear sensitivity level decline. The maximum sensitivity limit defines a lowest sensitivity level (e.g., maximum resolution) that linear sensitivity decline is allowed to reach. The sensitivity parameters are preprogrammed to fixed values and, over the operation of the IMD, are only modified (if at all) by a clinician.

In accordance with the sensitivity profile 153, when the CA signal 151 crosses the sensitivity profile 153 at starting point 155, the ORI process 136 treats the point 155 as a sensed R-wave and begins a refractory interval 159. No new R-wave (or T-wave) will be sensed during the refractory interval 159. At the end of the refractory interval 159, the sensitivity is adjusted to a threshold start sensitivity 161. The threshold start sensitivity 161 is defined as a percentage of the peak amplitude 163 of the QRS complex of the CA signal 151 detected during the refractory interval 159. The sensing circuit 144 maintains the threshold start sensitivity 161 for a decay delay time interval 169, after which the ORI process 136 begins to monotonically decrease the sensitivity (increase the resolution) of the sensing circuit 144 as denoted by the sensitivity decay 165 within the sensitivity profile 153. The sensing circuit 144 continues to decrease the sensitivity until either the sensitivity decay 165 reaches the maximum sensitivity 157 or an amplitude of the rectified cardiac activity signal 151 exceeds the sensor sensitivity profile 153, such as at a point 167 where a new sensed R wave is detected.

The sensitivity of the sensing circuit 144 (FIG. 2A) is continuously adjusted by the microcontroller 121 in accordance with the sensitivity profile 153 over the course of an individual cardiac event. However, the conventional ORI process does not modify the parameter settings of the sensitivity profile beat by beat or on demand sensitivity profile parameter In accordance with embodiments herein, the values of the sensitivity parameters may be adjusted based on whether the ORI process 136 is deemed to declare false AF detection R-waves. False AF detection may occur in connection with inappropriate R-wave sensing which may arise from under-sensing of R-waves and/or over-sensing of non-R-waves (e.g., noise, or P-waves, or T-waves as R-waves). For example, the confirmatory feature detection process 137 may determine when the ORI process 136 declares an undesirable number of false AF detections and in response thereto adjust one or more sensitivity profile parameters. Additionally, or alternatively, the confirmatory feature detection process may be implemented external to the ICM 100, such as at a local external device or remote server. The local external device and/or remote server may then return, to the ICM 100, adjustments to the sensitivity profile parameters when an externally implemented confirmatory feature detection process identifies an undesirable number of false AF detections.

Returning to FIG. 2A, the ICM 100 further includes an analog-to-digital A/D data acquisition system (DAS) 150 coupled to one or more electrodes via the switch 127 to sample cardiac activity signals across any pair of desired electrodes. The data acquisition system 150 is configured to acquire cardiac electrogram (EGM) signals as CA signals, convert the raw analog data into digital data, and store the digital data as CA data for later processing and/or telemetric transmission to an external device 154 (e.g., a programmer, local transceiver, or a diagnostic system analyzer). The data acquisition system 150 is controlled by a control signal 156 from the microcontroller 121. The EGM signals may be utilized as the cardiac activity data that is analyzed for potential AF episodes. The ACS adjustment and ORI process 136 may be applied to signals from the sensor circuit 144 and/or the DAS 150.

By way of example, the external device 154 may represent a bedside monitor installed in a patient's home and utilized to communicate with the ICM 100 while the patient is at home, in bed or asleep. The external device 154 may be a programmer used in the clinic to interrogate the ICM 100, retrieve data and program detection criteria and other features. The external device 154 may be a handheld device (e.g., smartphone, tablet device, laptop computer, smartwatch and the like) that can be coupled over a network (e.g., the Internet) to a remote monitoring service, medical network and the like. The external device 154 facilitates access by physicians to patient data as well as permitting the physician to review real-time CA signals while collected by the ICM 100.

The microcontroller 121 is coupled to a memory 160 by a suitable data/address bus 162. The programmable operating parameters used by the microcontroller 121 are stored in memory 160 and used to customize the operation of the ICM 100 to suit the needs of a particular patient. Such operating parameters define, for example, detection rate thresholds, sensitivity, automatic features, AF detection criteria, activity sensing or other physiological sensors, and electrode polarity, etc.

In addition, the memory 160 stores the cardiac activity data, as well as the markers and other data content associated with detection of arrhythmia episodes. The operating parameters of the ICM 100 may be non-invasively programmed into the memory 160 through a telemetry circuit 164 in telemetric communication via communication link 166 with the external device 154. The telemetry circuit 164 allows intracardiac electrograms and status information relating to the operation of the ICM 100 (as contained in the microcontroller 121 or memory 160) to be sent to the external device 154 through the established communication link 166. In accordance with embodiments herein, the telemetry circuit 164 conveys the cardiac activity data, markers and other information related to AF episodes.

The ICM 100 may further include magnet detection circuitry (not shown), coupled to the microcontroller 121, to detect when a magnet is placed over the unit. A magnet may be used by a clinician to perform various test functions of the housing 102 and/or to signal the microcontroller 121 that the external device 154 is in place to receive or transmit data to the microcontroller 121 through the telemetry circuits 164.

The ICM 100 can further include one or more physiologic sensors 170. Such sensors are commonly referred to as (in the pacemaker arts) as "rate-responsive" or "exercise" sensors. The physiological sensor 170 may further be used to detect changes in the physiological condition of the heart, or diurnal changes in activity (e.g., detecting sleep and wake states). Signals generated by the physiological sensors 170 are passed to the microcontroller 121 for analysis and optional storage in the memory 160 in connection with the cardiac activity data, markers, episode information and the like. While shown as being included within the housing 102, the physiologic sensor(s) 170 may be external to the housing 102, yet still be implanted within or carried by the patient. Examples of physiologic sensors might include sensors that, for example, activity, temperature, sense respiration rate, pH of blood, ventricular gradient, activity, position/posture, minute ventilation (MV), and so forth.

A battery 172 provides operating power to all of the components in the ICM 100. The battery 172 is capable of operating at low current drains for long periods of time. The battery 172 also desirably has a predictable discharge characteristic so that elective replacement time can be detected. As one example, the housing 102 employs lithium/silver vanadium oxide batteries. The batten 172 may afford various periods of longevity (e.g., three years or more of device monitoring). In alternate embodiments, the battery 172 could be rechargeable. See for example, U.S. Pat. No. 7,294,108, Cardiac event micro-recorder and method for implanting same, which is hereby incorporated by reference.

The ICM 100 provides a simple to configure data storage option to enable physicians to prioritize data based on individual patient conditions, to capture significant events and reduce risk that unexpected events are missed. The ICM 100 may be programmable for pre- and post-trigger event storage. For example, the ICM 100 may be automatically activated to store 10-120 seconds of CA data prior to an event of interest and/or to store 10-120 seconds of post CA data. Optionally, the ICM 100 may afford patient triggered activation in which pre-event CA data is stored, as well as post event CA data (e.g., pre-event storage of 1-15 minutes and post-event storage of 1-15 minutes). Optionally, the ICM 100 may afford manual (patient triggered) or automatic activation for CA data. Optionally, the ICM 100 may afford additional programming options (e.g., asystole duration, bradycardia rate, tachycardia rate, tachycardia cycle count). The amount of CA data storage may vary based upon the size of the memory 160.

The ICM 100 may provide comprehensive safe diagnostic data reports including a summary of heart rate, in order to assist physicians in diagnosis and treatment of patient conditions. By way of example, reports may include episodal diagnostics for auto trigger events, episode duration, episode count, episode date/time stamp and heart rate histograms. The ICM 100 may be configured to be relatively small (e.g., between 2-10 cc in volume) which may, among other things, reduce risk of infection during implant procedure, afford the use of a small incision, afford the use of a smaller subcutaneous pocket and the like. The small footprint may also reduce implant time and introduce less change in body image for patients.

Figure 2C:
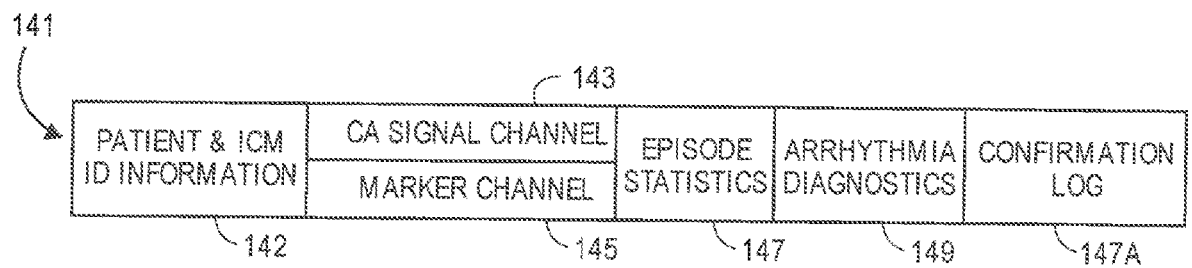
FIG. 2C illustrates cardiac activity data generated and stored by an ICM in accordance with embodiments herein.

FIG. 2C illustrates cardiac activity data generated and stored by the ICM 100 in memory 160 in accordance with embodiments herein. The CA data 141 is stored by the ICM in response to detection of episodes of interest, patient initiated instructions, physician initiated instructions and the like. The CA data 141 may include, among other things, patient and ICM identification information 142. By way of example, the patient identification information may include a patient unique medical record number or other identifier, patient name and/or patient demographic information. The ICM ID may include a serial number or other unique identifier of the ICM, software and firmware version numbers, and/or a unique wireless ID. The CA data 141 includes one or more signal channels 143 that store CA signals collected by a corresponding sensing channel (e.g., sensor circuit 144 or DAS 150). The CA signal channel 143 may include EGM signals for a series of cardiac beats/events sensed by the ICM. The CA data 141 also includes a marker channel 145 having, among other things, device documented markers identified by the ICM 100 in connection with the CA signal. The device documented markers within the marker channel 145 may include device documented markers indicative of normal sinus features, AF detected events, AF detected episodes and the like. For example, the ORI process 136 (FIG. 2A) utilizes the sensitivity profile 153 (FIG. 2B) to identify R-waves in the CA signal.

The content of the CA signal channel 143 and marker channel 145 may be displayed on a display of an external device (e.g., smart phone, tablet device, computer, smart watch, etc.) as corresponding types of CA and marker waveforms (e.g., in a rhythm display screen). In the present example, a single CA signal channel 143 is described in connection with a single CA signal. Optionally, embodiments herein may be implemented in connection with multiple CA signal channels. For example, the ICM 100 may be configured to include multiple sensing channels with different sensing characteristics. As one example, a first sensing channel may be configured to perform full range signal sensing, such as in connection with detecting R-waves (corresponding to the CA signal channel 143). A second sensing channel may be configured to perform narrow range signal sensing, such as in connection with detecting P-waves which have much smaller amplitude in comparison to the R-waves. Optionally, multiple ECG signals may be displayed in parallel and temporally aligned with EGM and marker waveforms.

The CA data 141 also includes episode statistics 147 and arrhythmia diagnostics 149. The episode statistics 147 may be presented in a window on a user interface to list various statistical data for any or all episodes recorded by the ICM 100 since the episode and CA data storage were last cleared. Optionally, the episode statistics 147 may also list the number of inhibited VT diagnoses due to arrhythmia qualifiers, such as a bigeminal rhythm qualifier, and/or other rhythm discriminators. As further nonlimiting examples, the episode statistics 147 may also include a date of a last programmer session, date of the last ICM interrogation, the date of the presently stored episodes and the date when EGMs were last cleared from the ICM and the like.

Figure 2E:
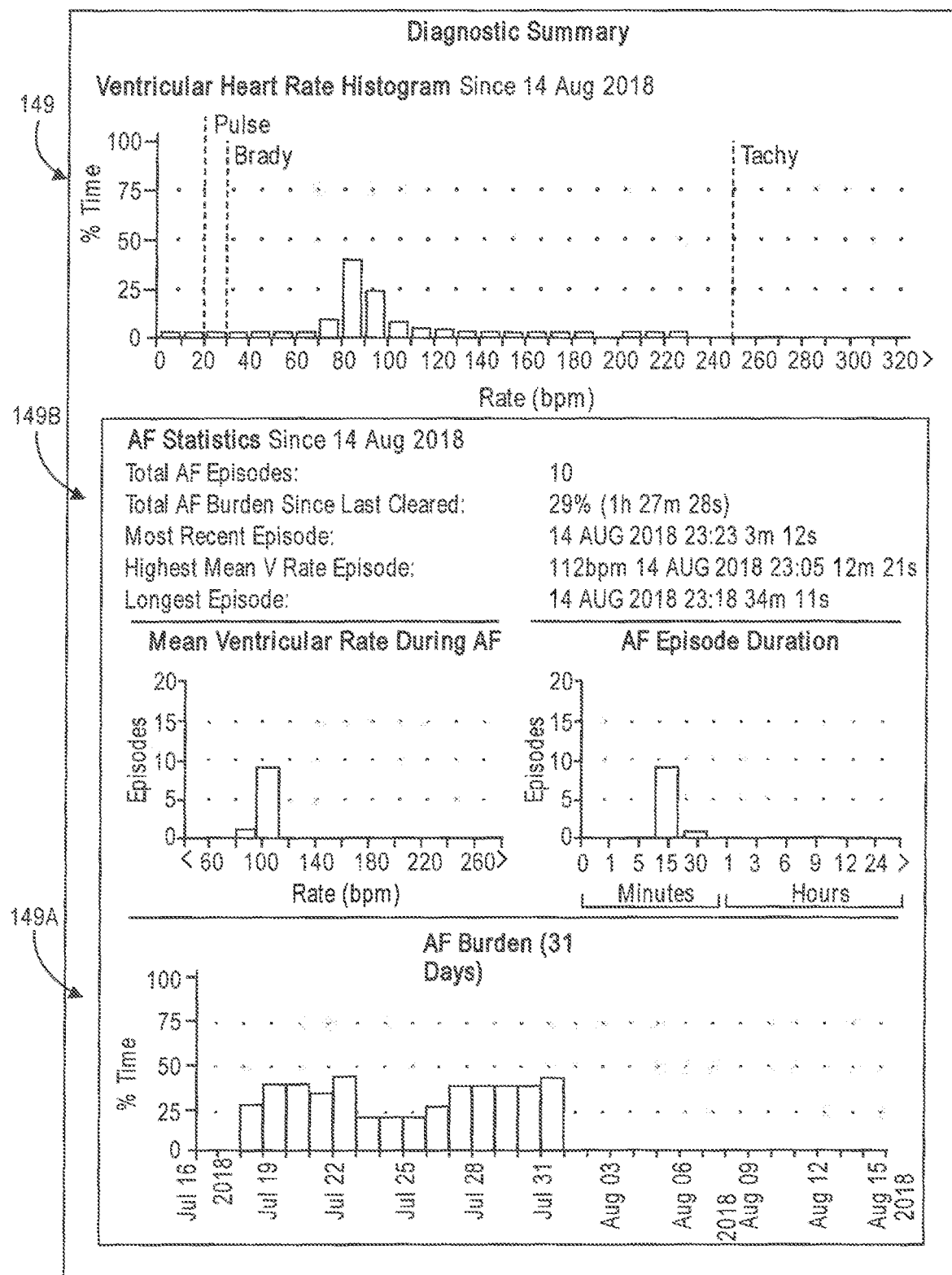
FIG. 2E illustrates screenshots of displays in which episode statistics and arrhythmia diagnostics may be presented to a physician in accordance with an embodiment herein.

FIGS. 2D and 2E illustrate screenshots of displays in which episode statistics and arrhythmia diagnostics may be presented to a physician in accordance with an embodiment herein. The arrhythmia diagnostics 149 may represent cumulative diagnostic information for a period of time, such as when the diagnostics data is last cleared from the ICM. The arrhythmia diagnostics 149 may include various information concerning heart rate, such as ventricular heart rate histograms, dates and times of last programmer sessions, diagnostic data last read, diagnostic data last cleared and the like. The arrhythmia diagnostics 149 may also include AF diagnostics, such as AF burden 149A, AF summaries, AF statistical data 149B, dates and times of last programmer session, last time the AF diagnostic data were read, last time the AF diagnostic data was cleared and the like. By way of example, AF burden may be displayed in an AF diagnostics window of a computing device formatted as one or more bar graphs of a percentage of time (as shown in FIG. 2E) that the patient experienced AF during a predetermined period of time (e.g., each day, each week, each month). The AF burden may show a percentage of time that the patient was in AF since the AF diagnostics data were last cleared. The AF summary may include one or more graphs of mean ventricular heart rate and a duration of AF episodes since the AF diagnostic data were last cleared. The AF diagnostic data may accrue various cumulative totals concerning AF episodes detected and/or stored since the AF diagnostic data were last cleared. The AF statistics may include, among other things, a total number of AF episodes, AF burden trends, AF episode duration histograms, mean ventricular rate during AF and the like.

As explained herein, an enhanced confirmatory AF detection process is implemented to analyze the results of the baseline analysis performed by the ORI process in the ICM. The enhanced confirmatory AF detection process determines whether AF episodes declared by the ICM are true or false, and updates the AF diagnostics in connection there with. Next, various processes are described in connection with embodiments herein that are performed by one or more of the circuits, processors and other structures illustrated in the figures and described in the specification.

FIG. 3 shows a high-level workflow for an enhanced confirmatory AF detection process implemented in accordance with embodiments herein. By way of example, the operations of FIG. 3 may be implemented, as a confirmatory process, where cardiac activity signals have been previously analyzed by an AF detection module, such as the ORI process described in connection with FIGS. 2A and 2B. The process may initiate the operations of FIG. 3 in an attempt to verify whether one or more episodes in a CA data set, are in fact an AF episode or a normal rhythmic/sinus episode. Optionally, the operations of FIG. 3 may be implemented in connection with a CA data set that has not been previously analyzed for potential AF episodes. The operations of FIG. 3 may be implemented as part of a local or distributed system, such as by the microcontroller 121 of the ICM, by a local external device and/or a remote server.

At 302, one or more processors of the system obtain a cardiac activity (CA) data set including CA signals recorded in connection with a series of cardiac events. The CA data includes device documented arrhythmic markers including identifying AF entry and/or exit within the series of cardiac events. The CA data also includes device documented rhythmic markers (e.g., R-wave) to identify the cardiac beats sensed by the device within the series of cardiac events. The CA data also include device documented activity and noise markers to identify periods of time under significant physical activity and/or noise interrupt within the series of cardiac events. All device documented markers are declared and designated by the ICM utilizing the ORI process to analyze the CA signals.

For example, the cardiac activity data may be obtained by an external monitoring device or ICM that includes electrodes that sense CA signals, such as electrocardiogram (ECG) signals and/or intra-electrocardiogram (EGM) signals. The ECG and/or EGM signals may be collected by a subcutaneous ICM that does not include a transvenous lead or otherwise experiences difficulty in sensing P-waves and/or R-waves. The cardiac activity data may have been previously acquired and stored in memory of an implantable or external monitoring device, implantable or external therapy delivery device, programmer, workstation, healthcare network or other system. When the cardiac activity data has been previously acquired, the obtaining operation at 302 represents accessing and reading the previously stored cardiac activity data.

The operations of FIG. 3 may be staged to be performed upon the CA data at various times, such as in real time (e.g., during or shortly after a patient experiences an episode) or at any time after storage of the CA data. The operations of FIG. 3 may be performed by devices and systems at various proximity to a patient with the ICM. For example, the CA data may be read out of an ICM and transmitted to a local portable external device (e.g., smartphone, table computer, laptop computer, smartwatch, etc.), where the local portable external device locally implements all or a portion of the operations described in connection with FIG. 3 while in close proximity to the patient. Additionally, or alternatively, the CA data may be read out of the ICM to a local portable external device and transmitted to a remote server, medical network, physician computer and the like, which implements all or a portion of the operations described in connection with FIG. 3 remote from the patient. Additionally, or alternatively, the CA data may be read from the ICM by a programmer device, such as during a patient visit to a physician, where the programmer device implements all or a portion of the operations described in connection with FIG. 3 during or after a patient-doctor visit.

The CA data may include CA signals for a series of cardiac events spanning over various periods of time. As one example, one segment or set of the cardiac activity data may be collected for an interval that is 30 seconds to 5 minutes in length and that includes one or more ICM declared AF episodes. As another example, one segment or set of the cardiac activity data may be collected for an interval that begins 10-60 seconds before an episode of interest (e.g., an AF episode) and that ends 10-60 seconds after the episode of interest. A CA data set may include one or multiple AF episodes. The duration of a CA data set may be programmed for a predetermined period of time based on detection of AF episodes and/or based on other criteria. The predetermined period of time may be programmed by a clinician, or automatically updated by one or more processors throughout operation. By way of example, the predetermined period of time may correspond to one minute, 30 minutes, one hour or otherwise. The CA data obtained at 302 may correspond to one detected AF episode and/or multiple detected AF episodes. The CA data set obtained at 302 may correspond to one continuous series of cardiac events (e.g., 1 continuous series for 30 seconds to 5 minutes) and/or separate sets of cardiac events (3-10 separate series, each for 30 seconds to 3 minutes of cardiac events).

Collection and analysis of CA signals by the ICM may be initiated automatically when the ICM detects an episode of interest. Additionally, or alternatively, the ICM may collect and analyze CA signals in response to a user-initiated instruction. For example, a user may utilize a smart phone or other portable device to establish a communications session with the ICM and instruct the ICM to begin to collect and analyze cardiac signals, such as when the patient is experiencing discomfort, feeling faint, a rapid heart rate, etc.

At 304 to 320, the one or more processors determine whether the on-board RR interval irregularity process (implemented by the ICM_declared one or more false positive AF episodes, such as due to under-sensing or over-sensing features within the CA signal. The operations at 304 to 320 generally perform an R-wave enhancement and feature rejection (EFR) process. The EFR process enlarges or exaggerates features of interest (e.g., R-wave) within the CA signal and optionally suppresses at least certain features not of interest (e.g., non-R-wave features such as noise, T-waves) to obtain confirmatory feature markers. The EFR process applies a series of tests to confirm or reject alternative conditions that a patient may have experienced. The operations at 306 to 320 confirm or reject a presence or absence of certain rhythmic, physiologic and non-physiologic (e.g., noise) features within the CA data. Non-limiting examples of the features, for which the process searches include noise, R-wave changes, P-waves, and post ventricular contractions.

At 304, the one or more processors analyze the CA data for noise and pass or remove segments of the CA signal for select cardiac events based on a noise level within the corresponding segment of the CA signal. The noise is identified based on noise discrimination parameters that are set to a desired sensitivity level. While the sensitivity of the noise detection process at 304 may be adjusted, the sensitivity of the noise detection process at 304 is more selective than the on-board noise detection circuit in the ICM. For example, at 304, the one or more processors may implement the noise detection process described in one or more of the Co-Pending Related Applications referred to above, filed concurrently on the same day as the present application. For example, the operation at 304 generally represents a software based evaluation of the CA data to detect noise. The software based evaluation can be developed in a manner that is tailored to AF detection such that the software-based noise rejection is mare sensitive in connection with identifying or removing unduly noisy CA signal segments that in turn give rise to inappropriate R-wave detection, leading to false AF episodes declaration by the ICM. The original CA data processed in connection with FIG. 3 results from the onboard ORI process of the ICM. The onboard ORI process processes incoming signals that have first passed through a hardware-based noise detect that applies noise discrimination the hardware-based noise detector is not as sensitive as, and not as adaptable as, the software based noise discrimination implemented at 304. Also, depending upon a complexity of the software-based noise discrimination, processors of an ICM may not have a sufficient processing power to implement the software noise discrimination. The extent to which the software-based noise discrimination may be implemented on an ICM depends in part upon the sensitivity level desired. For example, the discrimination parameters may be set to a very "conservative" level such that the noise detector only eliminates CA signals for cardiac events that include a substantial amount of noise (e.g., the signal to noise ratio is less than or equal to 50%). Levels for the noise discrimination parameters may be adjusted to eliminate more cardiac events that include relatively intermediate levels of noise (e.g., the signal to noise ratio is between 75% and 90%). The noise discriminator passes CA signals for cardiac events that have less noise than the level defined by the noise discrimination parameters.

Optionally, at 304, when the noise level is sufficiently high (e.g., satisfying a threshold), the initial AF diagnosis/declaration by the ICM may be overridden. For example, when the noise level exceeds a threshold in connection with an AF episode declared by the ICM, the processors may cancel the AF episode declaration and reset any counters set in connection there with.

At 306, the one or more processors apply a feature enhancement process to form modified CA signals in which sinus features of interest are enlarged or exaggerated relative to the original/baseline CA signals. Optionally, at least certain features not of interest (e.g., noise, T-waves) are reduced or suppressed relative to the baseline CA signals in order to generate the confirmatory feature (e.g., R-wave) marker. For example, at 306, the one or more processors may implement the feature enhancement process described in one or more of the Co-Pending Related Applications referred to above, filed concurrently on the same day as the present application.

At 307, the one or more processors analyze the modified CA signal utilizing a confirmatory feature detection process. For example, at 306, the one or more processors may implement, as the confirmatory feature detection process, the R-wave detection processes described in one or more of the Co-Pending Related Applications referred to above, and filed concurrently on the same day as the present application. The processors analyze the modified CA signal to identify R-waves, and store a set of confirmatory feature markers separate and distinct from the device documented (DD) feature markers.

At 308, the one or more processors determine whether the confirmatory feature markers match or differ from the DD feature markers. For example, the determination at 308 may be based on a simple count of the number of DD feature markers as compared to a count of the number of confirmatory feature markers. Additionally, or alternatively, the determination at 308 may determine whether the confirmatory feature detection process identified confirmatory feature markers (e.g., R-waves) from the CA signals that were not identified by the ORI process or displaced significantly. For example, the DD and confirmatory feature markers for the CA data may be aligned temporally and compared to identify differences.

Differences may occur due to various reasons. For example, the ORI process may under-sense R-waves, while the confirmatory feature detection process properly identifies a feature of interest in the modified CA signal as an R-wave. As another example, the ORI process may over sense R-waves, while the confirmatory feature detection process properly determines that no R-wave is present in a particular segment of the CA signal. Additionally, or alternatively, a difference may be declared when the ORI process and confirmatory feature detection process both declare an R-wave for a specific cardiac event, but the DD and confirmatory R-waves are temporally offset from one another in time by more than a desired R-wave offset threshold.

When the process determines at 308 that a difference or change exists between the confirmatory and DD feature markers, flow moves to 310. When the process determines that no difference or change exists between the confirmatory and DD feature markers, flow moves to 312. At 310 the one or more processors identify instability in the confirmatory feature markers. At 310, the one or more processors determine whether the instability within the confirmatory feature marker indicates AF. The processors determine the presence or absence of instability by analyzing variation in the RR intervals between the confirmatory features markers, such as using the processors described in the Co-Pending Related Application and/or the '456 patent. If the instability/variation equals or is below a stability threshold, the segment of the CA signal is considered to exhibit a stable feature-to-feature interval that does not indicate AF. Consequently, flow moves to 316. Alternatively, when the instability is above the instability threshold, the analysis of the CA signal segment is considered to exhibit an unstable feature-to-feature interval. Consequently, flow moves to 312.

At 316, when AF is not indicated, the one or more processors classify an episode in the CA data set to be a DD false positive or false detection. At 316, the one or more processors may perform additional operations, such as setting one or more flags to track the declaration of DD false positives by the ORI process on the ICM. Additionally, or alternatively, at 316, the one or more processors may reverse a diagnosis of AF, adjust various statistics tracking the patient's behavior and the like. For example, the AF diagnostics (e.g., 149 in FIG. 2C) may be updated to correct for false AF detection. Additionally, or alternatively, a memory segment within the ICM that includes the CA data set associated with a false AF detection may be set to have a lower priority. Reassignment of priority levels to different memory segments may be utilized in connection with over-writing memory segments during future use. For example, when the CA data memory of the ICM approaches or becomes full, the memory segment assigned the lowest priority may then be overwritten first when the ICM detects new AF episodes.

When flow advances to 312, the potential still exists that the CA signals does not include an AF episode. Therefore, the process of FIG. 3 performs additional analysis upon the CA data. At 312, the one or more processors perform a P-wave detection operation to determine whether P-waves are present within the CA signal segment being analyzed. For example, at 312, the one or more processors may implement the P-wave detection process described in one or more of the Co-Pending Related Applications referred to above, and filed concurrently on the same day as the present application. When a P-wave is identified to be present in the CA signal, the process determines that the presence of a P-wave indicates that the current episode is not an AF episode even though RR interval irregularity may be present. Accordingly, flow moves to 316.

Alternatively, at 312 when the one or more processors determine that no P-waves are present within the CA signal, a potential still remains that the CA signal does not correspond to an AF episode. Accordingly, flow advances to 318 where additional analysis is applied to the CA data set. At 318, the one or more processors apply a morphology based premature ventricular contraction (PVC) detection operation. For example, at 318, the one or more processors may implement the QRS complex morphology based PVC detection process described in one or more of the Co-Pending Related Applications referred to above, and filed concurrently on the same day as the present application. The processors determine whether a QRS complex morphology has varied beyond a morphology variation threshold. Variation in the R-wave morphology beyond the morphology variation threshold provides a good indicator that the cardiac events include one or more PVC. When the cardiac events include a sufficient number of PVCs, the process may attribute an R-R interval variation to (and indicative of) PVCs or non-atrial originated beats that lead to significantly different R-R intervals, and not due to (or indicative of) an AF episode. Accordingly, when the R-wave morphology exceeds the morphology variation threshold, flow returns to 316, where the process performs the operations described herein. At 316, one or more flags may be set to indicate that the false AF detection was declared due to one or more PVCs present within the CA data. Additionally, or alternatively, a diagnosis may be changed from AF episode to PVC episode. The number of PVC may vary that are needed to achieve an R-wave morphology variation at 318 sufficient for flow to branch to 316 (e.g., declare a false AF detection).

At 318, alternatively, when the R-wave morphology does not exceed the morphology variation threshold, the process interprets the condition as an indicator that the cardiac events do not include significant number of PVCs. Thus, flow moves to 320. At 320, the one or more processors confirm a device documented AF episode and records the current episode to remain as originally declared by the ORI process.

Optionally, the sequence of operations discussed in connection with FIG. 3 may be changed and/or some of the operations may be omitted depending on computational and performance objectives. For example, it may be determined that a low probability exists that a particular patient (or ICM) experiences PVCs that cause false AF detection, and thus, the process of FIG. 3 may omit the PVC detection operation at 318. Additionally, or alternatively, it may be determined that a low probability exists that an ICM is incorrectly detecting P-waves as R-waves that would cause false AF detection, and thus, the process of FIG. 3 may omit the P-wave detection operation at 312.

Additionally, or alternatively, it may be determined that less processing time/power is utilized to identify P-waves (operations at 312) and/or PVCs (operations at 318) that cause false AF detection, as compared to R-wave detection and analysis of RR interval stability (operations at 306-310). Accordingly, the P-wave and/or PVC detection operations may be performed before the R-wave detection and analysis. In the present example, in the event a P-wave or PVC is detected, the process may declare a CA data set to include a false AF detection without performing the further computations for R-wave detection and analysis.

Optionally, the operations at 308-318 may be modified to not represent binary branches between alternative paths. Instead, the decisions at operations 308-318 may result in a score or a vote, rather than a binary "AF" or "not AF". The vote or score may be variable based upon a degree to which the feature of interest in the confirmatory analysis matches the determination from the original ORI process. Additionally, or alternatively, the vote or score may be based on a degree to which the feature of interest from the confirmatory analysis matches one or more baseline values. The votes or scores may be used in conjunction with other AF detection algorithms in order to find a probability that an AF episode has occurred.

The operations of FIG. 3 may be repeated periodically or in response to detection of particular criteria, such as detection of potential atrial fibrillation episodes or otherwise.

The operations of FIG. 3 afford a powerful, sophisticated process to confirm AF detection within ECG and EGM signals in a non-real time manner. The AF detection confirmation processes described herein may utilize computationally expensive analysis that may otherwise not be to be implemented in an on-board circuit within an ICM, either due to memory and power constraints, processing power constraints, and/or an inability to complete the analysis in real time.

Optionally, the operations of one or more of the stages within the process of FIG. 3 may be adapted to run in ICM firmware, although firmware implementations may exhibit different overall performance. In a firmware implementation, a similar form of step-by-step discrimination on existing AF episodes may be achieved. Alternatively, some or all of the features may be adapted for real-time use and set as additional or alternative signals. For example, the determinations at 306-318 may produce factors that are applied to an AF probability and sudden onset determination as AF detection criteria.

FIG. 4 illustrates a flow chart for classifying AF detection and developing recommendations for sensitivity profile parameter settings in accordance with embodiments herein. For example, the operations of FIG. 4 may be performed at 316 and/or 320 in FIG. 3 and/or at other points in the processes described herein. The operations of FIG. 4 build and/or add to a confirmation log that tracks and records the differences and similarities between the results of the EFR and ORI processes. The confirmation log may be stored together with, or separate from, the underlying baseline CA data set and/or the modified CA data set. Optionally, the confirmation log may not represent a separate file, but instead merely represent parameter settings or other information appended to the original or modified CA data set. For example, the confirmation log may be saved as metadata or otherwise appended to the CA data set.

At 402, the one or more processors of the system determine whether the EFR process identified one or more false AF detection by the ORI process applied by the ICM. When the EFR process and the ORI process detect a common or similar number/degree of AF episodes in the CA data set, flow moves to 404. At 404, the one or more processors record a match between the results of the EFR and ORI processes. The match is stored in the confirmation log. When the EFR process identifies a false AF detection that was declared by the ORI process, flow moves to 406.

At 406, the one or more processors classify the false AF detection into one of multiple different categories. Non-limiting examples of the categories include noise, inappropriate sensing, irregular sinus rhythm, frequent PVCs and the like. The processors may classify the false AF detection as noise when the baseline CA data set is determined to have an excessive amount of noise (at 302). For example, the excessive amount of noise may be determined when a number of cardiac events that are removed/suppressed (at 304, 312, 318) exceeds a threshold and/or exceeds a percentage of the total number of cardiac events in the CA data set. The processors may classify the false AF detection as inappropriate sensing when the feature detection (at 306) determines that the CA data includes more or few features of interest (e.g., under-sensed R-waves or over-sensed false R-waves). The processors may classify the false AF detection as sinus rhythm when the P-wave detection (at 312) determines that the CA data set includes one or more P-waves. The processors may classify the false AF detection as frequent PVCs when the PVC detection (at 318) determines that the CA data exceeds a PVC threshold.

At 408, the one or more processors record the classification identified at 406 in the confirmation log. At 410, the one or more processors determine whether additional guidance is to be provided for setting sensitivity profile parameters of the ICM. For example, the processors, at 410, may determine whether an extent or degree of the false R-wave and AF detection (e.g., number of under-sensed R-waves, number of P-waves (as well as T-wave or noise artifact) classified as R-waves, number of frequent PVCs) exceeds a threshold that justifies adjusting one or more sensitivity profile parameters of the ICM. When sensitivity profile parameter adjustments can be made, flow moves to 412. Otherwise, flow continues to 414.

When the extent or degree of the false R-wave and AF detection warrants a parameter adjustment, the sensitivity profile parameter adjustment is determined based in part on the classification at 406. At 412, the one or more processors declare an adjustment to the sensing parameters based on a nature and/or extent of the false R-wave and AF detection. For example, when a false AF detection is classified as due to inappropriate sensing, the processors may declare the sensitivity profile parameter adjustment to be an increase or decrease in the feature (e.g., R-wave) detection threshold. As another example, the processors may declare the sensitivity profile parameter adjustment to be an increase in the R-wave detection threshold when P-waves are identified as R-waves by the ORI process. As another example, the processors may declare the sensitivity profile parameter adjustment to be an increase in the decay delay value when the ORI process over-senses T-waves and designates the T-waves to be R-waves. The sensitivity profile parameter adjustment is saved in the confirmation log. Optionally, the confirmation log may also maintain a PVC count.

The increase or decrease in the sensitivity profile parameter adjustment may be a predefined step (e.g., increase threshold by X mV or Y %). Optionally, the increase or decrease may be based on an extent or nature of the false R-wave and AF detection. For example, when the ORI process under-sensed multiple R-waves in the CA data set, the process may decrease the R-wave detection threshold by a larger factor as compared to when the ORI process under-senses one or a few R-waves out of multiple R-waves. As another example, a decay delay value adjustment and/or refractory period value adjustment may be determined based in part on a number of T waves sensed as R-waves, a timing between the T waves and corresponding preceding R-waves, and/or a peak amplitude of the T waves relative to the sensing sensitivity at the time the T-wave is detected.

Optionally, the one or more processors may identify additional or alternative sensitivity profile parameter adjustments based on a database of sensitivity profile parameter settings that are correlated to cardiac activity data for a patient population. For example, a database may be maintained of EGM or ECG data segments collected in connection with numerous patients that experienced AF, sinus rhythms and/or other arrhythmias, where the EGM/ECG data segments are correlated with sensitivity profile parameter settings that are used by a monitoring device to collect the EGM or ECG data. The patient population database may also indicate which sensitivity profile parameter settings achieved desired results and which sensitivity profile parameter settings did not achieve desired results. The database may further include quality indicators indicative of whether the sensitivity profile parameter settings were deemed to collect good or accurate results (e.g., correctly sense R-waves without over-sensing P-waves or T waves, and correctly sense all R-waves without under-sensing of R-waves with smaller amplitude). The database may further include quality indicators indicative of whether the sensitivity profile parameter settings were deemed to accurately declare AF detection in a high percentage of the instances of AF. The quality indicators may be automatically entered based on automated analysis of the data within the database and/or entered by physicians or other medical personnel as sensitivity profile parameter settings are adjusted for individual patients. The database may be available on a medical network, through a cloud computing service and/or other local or remote source.

At 414, the one or more processors compare the current false AF detection, modified CA data set and/or baseline CA data to a database of third-party CA data sets and false/valid AF detections for other patients. The processors may identify matches or similarities between the false/valid AF detection, modified CA data set and/or baseline CA data set, for the current patient, and the corresponding type of AF detections and third-party CA data set from the database of the larger population. When no match occurs, the operations of FIG. 4 end. Alternatively, when one or more matches occur between the current CA data set and the patient population database, flow moves to 416. At 416, the one or more processors identify additional or alternative sensitivity profile parameter adjustments to record in the confirmation log for the present patient based on the matches or similar cases from the database and the present patient.

The sensitivity profile parameter adjustments, in the confirmation log, may be presented on a display of a mobile device, computer, workstation, etc., as a suggestion or option ICM for the physician or other medical personnel to apply to a current. Optionally, the sensitivity profile parameter adjustments may be pushed and uploaded to the ICM from a local portable external device and/or a remote medical network. The sensitivity profile parameter adjustments may be pushed to the ICM at the direction of the physician or other medical personnel, after the physician or medical personnel has reviewed the baseline and/or modified CA data (with R-wave and AF markers) and other statistical information concerning one or more episodes experienced by the patient. Additionally, or alternatively, the sensitivity profile parameter adjustments may be automatically pushed and uploaded to the ICM at the conclusion of the operations of FIG. 4, such as when the adjustment is within a predetermined limit.

Figure 5:
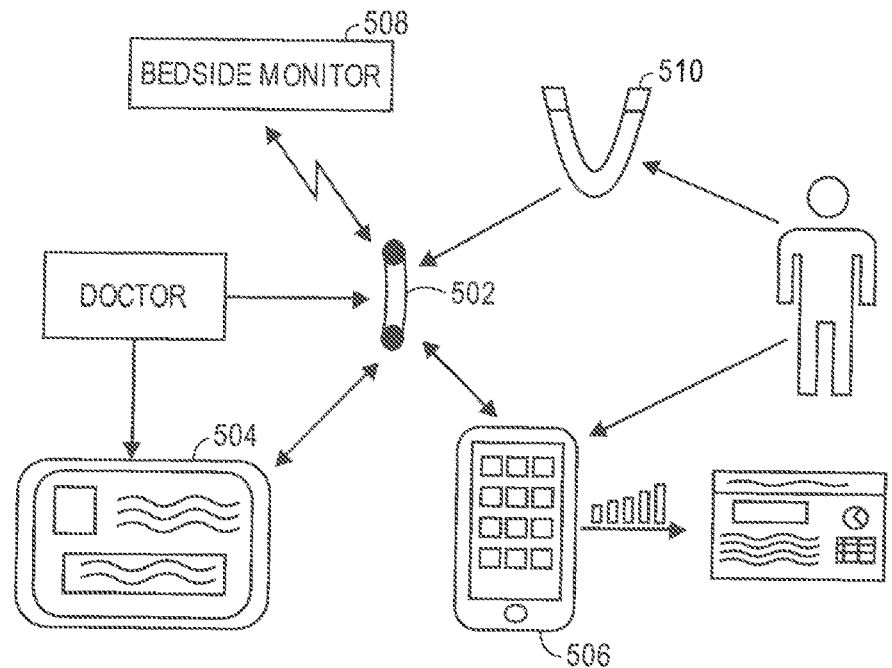
FIG. 5 illustrates a system level diagram indicating potential devices and networks in which the methods and systems herein may be utilized in accordance with embodiments herein.

FIG. 5 illustrates a system level diagram indicating potential devices and networks that utilize the methods and systems herein. For example, an implantable cardiac monitoring device (ICM) 502 may be utilized to collect a cardiac activity data set. The ICM 502 may supply the CA data set (CA signals and DD feature markers) to various local external devices, such as a tablet device 504, a smart phone 506, a bedside monitoring device 508, a smart watch and the like. The devices 504-508 include a display to present the various types of CA signals, markers, statistics, diagnostics and other information described herein. The ICM 502 may convey the CA data set over various types of wireless communications links to the devices 504, 506 and 508. The ICM 502 may utilize various communications protocols and be activated in various manners, such as through a Bluetooth, Bluetooth low energy, WiFi or other wireless protocol. Additionally, or alternatively, when a magnetic device 510 is held next to the patient, the magnetic field from the device 510 may activate the ICM 502 to transmit the cardiac activity data set and AF data to one or more of the devices 504-508.

The processes described herein for analyzing the cardiac activity data and/or confirm AF detection may be implemented on one or more of the devices 504-508. Additionally, or alternatively, the ICM 502 may also implement the confirmatory processes described herein. The devices 504-508 may present the CA data set and AF detection statistics and diagnostics to clinicians in various manners. As one example, AF markers may be illustrated on EGM signal traces. AF and sinus markers may be presented in a marker channel that is temporally aligned with original or modified CA signals. Additionally, or alternatively, the duration and heart rate under AF may be formatted into histograms or other types of charts to be presented alone or in combination with CA signals.

Figure 6:
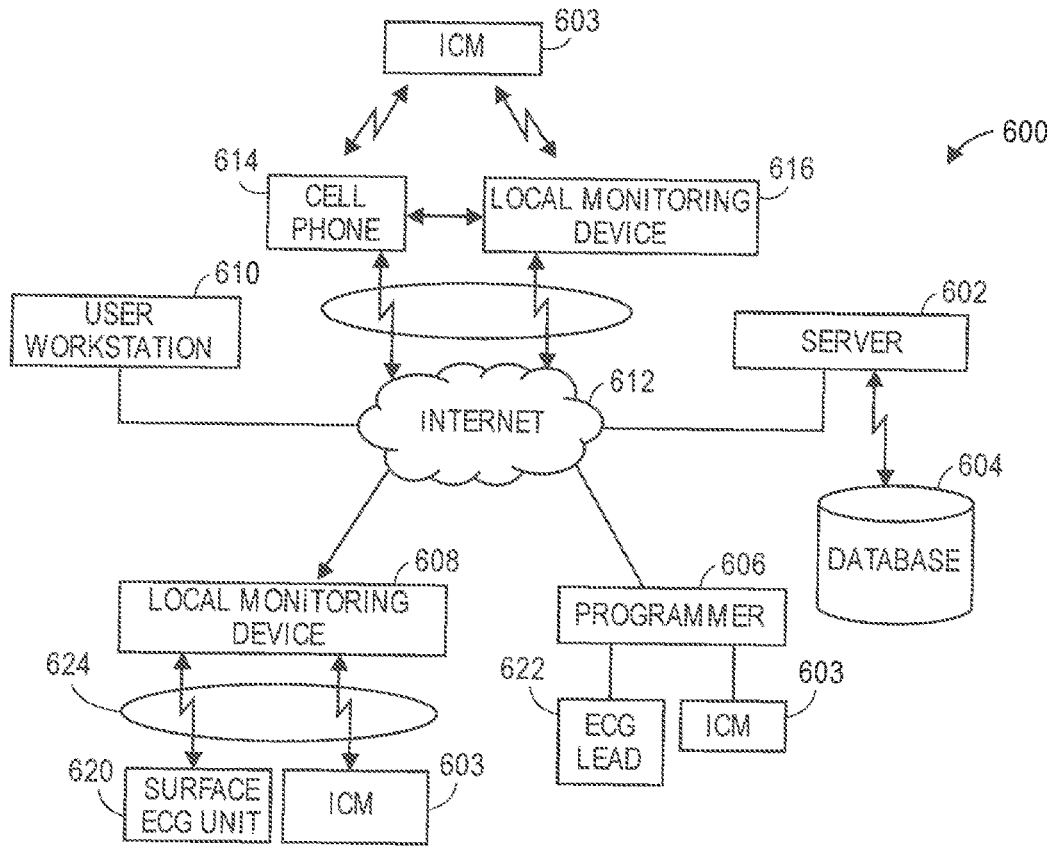
FIG. 6 illustrates a distributed processing system in accordance with embodiments herein.

FIG. 6 illustrates a distributed processing system 600 in accordance with embodiments herein. The distributed processing system 600 includes a server 602 connected to a database 604, a programmer 606, a local monitoring device 608 and a user workstation 610 electrically connected to a network 612. Any of the processor-based components in FIG. 6 (e.g., workstation 610, cell phone 614, local monitoring device 616, server 602, programmer 606) may perform the processes discussed herein.

The network 612 may provide cloud-based services over the Internet, a voice over IP (VoIP) gateway, a local plain old telephone service (POTS), a public switched telephone network (PSTN), a cellular phone based network, and the like. Alternatively, the communication system 612 may be a local area network (LAN), a medical campus area network (CAN), a metropolitan area network (MAN), or a wide area network (WAM). The communication system 612 serves to provide a network that facilitates the transfer/receipt of data and other information between local and remote devices (relative to a patient). The server 602 is a computer system that provides services to the other computing devices on the network 612. The server 602 controls the communication of information such as cardiac activity data sets, bradycardia episode information, asystole episode information, AF episode information, markers, cardiac signal waveforms, heart rates, and device settings. The server 602 interfaces with the network 612 to transfer information between the programmer 606, local monitoring devices 608, 616, user workstation 610, cell phone 614 and database 604. The database 604 stores information such as cardiac activity data, AF episode information, AF statistics, diagnostics, markers, cardiac signal waveforms, heart rates, device settings, and the like, for a patient population. The information is downloaded into the database 604 via the server 602 or, alternatively, the information is uploaded to the server 602 from the database 604. The programmer 606 may reside in a patient's home, a hospital, or a physician's office. The programmer 606 may wirelessly communicate with the ICM 603 and utilize protocols, such as Bluetooth, GSM, infrared wireless LANs, HIPERLAN, 3G, satellite, as well as circuit and packet data protocols, and the like. Alternatively, a telemetry "wand" connection may be used to connect the programmer 606 to the ICM 603. The programmer 606 is able to acquire ECG from surface electrodes on a person (e.g., ECGs) 622, electrograms (e.g., EGM) signals from the ICM 603, and/or cardiac activity data, AF episode information, AF statistics, diagnostics, markers, cardiac signal waveforms, atrial heart rates, device settings from the ICM 603. The programmer 606 interfaces with the network 612, either via the Internet, to upload the information acquired from the surface ECG unit 620, or the ICM 603 to the server 602.

The local monitoring device 608 interfaces with the communication system 612 to upload to the server 602 one or more of cardiac activity data set, AF episode information, AF statistics, diagnostics, markers, cardiac signal waveforms, heart rates, sensitivity profile parameter settings and detection thresholds. In one embodiment, the surface ECG unit 620 and the ICM 603 have a bi-directional connection 624 with the local RF monitoring device 608 via a wireless connection. The local monitoring device 608 is able to acquire cardiac signals from the surface of a person, cardiac activity data sets and other information from the ICM 603, and/or cardiac signal waveforms, heart rates, and device settings from the ICM 603. On the other hand, the local monitoring device 608 may download the data and information discussed herein from the database 604 to the surface ECG unit 620 or the ICM 603.

The user workstation 610 may be utilized by a physician or medical personnel to interface with the network 612 to download cardiac activity data and other information discussed herein from the database 604, from the local monitoring devices 608, 616, from the ICM 603 or otherwise. Once downloaded, the user workstation 610 may process the CA data in accordance with one or more of the operations described above. The user workstation 610 may upload/push settings (e.g., sensitivity profile parameter settings), ICM instructions, other information and notifications to the cell phone 614, local monitoring devices 608, 616, programmer 606, server 602 and/or ICM 603. For example, the user workstation 610 may provide instructions to the ICM 603 in order to update sensitivity profile parameter settings when the ICM 603 declares too many false AF detections.

The processes described herein in connection with analyzing cardiac activity data for confirming or rejecting AF detection may be performed by one or more of the devices illustrated in FIG. 6, including but not limited to the ICM 603, programmer 606, local monitoring devices 608, 616, user workstation 610, cell phone 614, and server 602. The process described herein may be distributed between the devices of FIG. 6.

Figure 7:
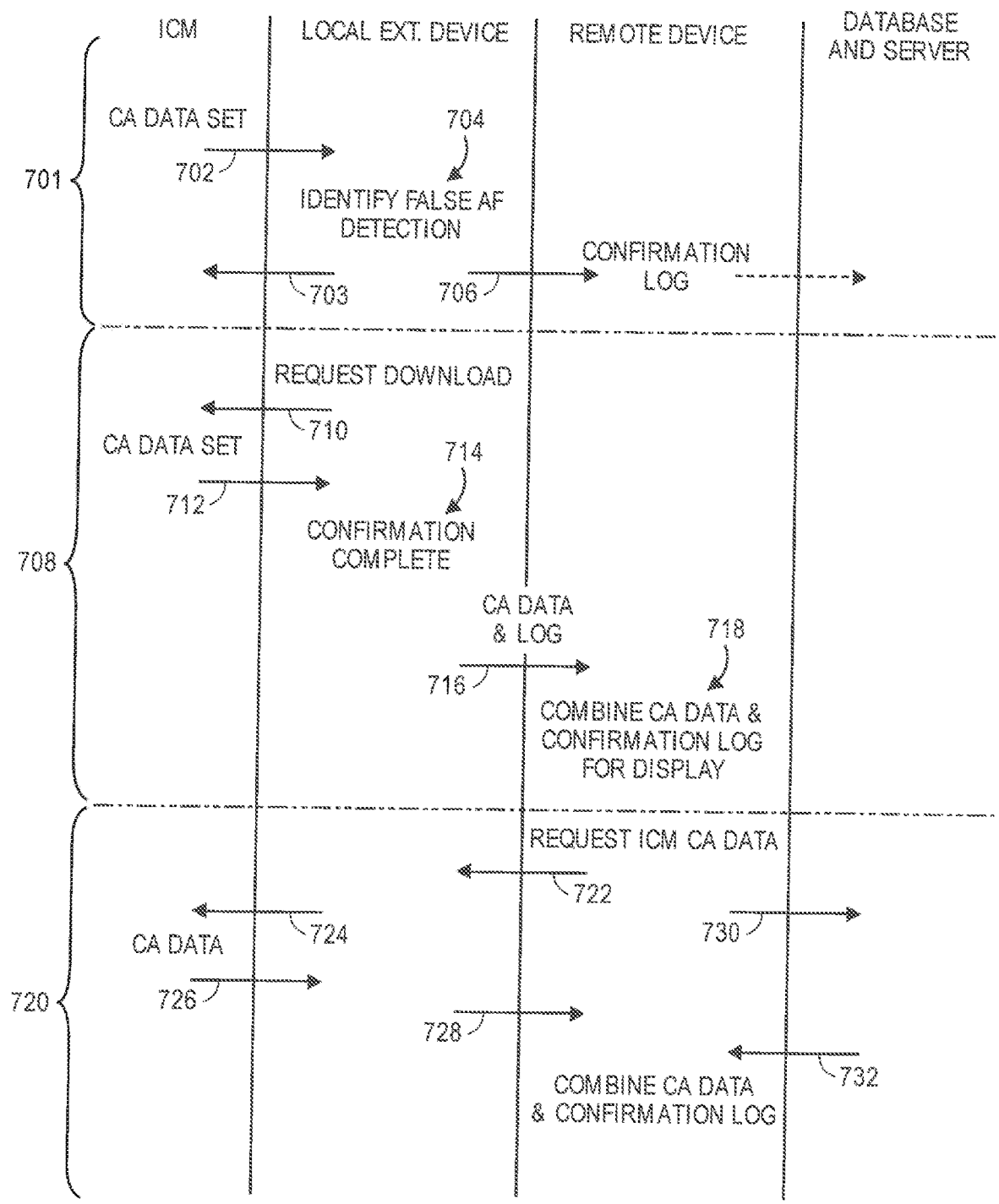
FIG. 7 illustrates a collection of communications between the ICM, a local device, a remote device and a server/database in accordance with embodiments herein.

FIG. 7 illustrates examples of communication sessions between the ICM, a local external device, a remote device and a server/database in accordance with embodiments herein. For convenience, reference is made to the devices of FIGS. 5 and 6, in connection with FIG. 7. For example, the local device may represent a cell phone 614, smart phone 506, bedside monitor 508 or local monitoring device 608, 616, while the remote device may represent a workstation 610, programmer 606, or tablet device 504.

During an AF detection and confirmation session 701, at 702, an ICM 100 provides a CA data set to a local device. At 704, the local device utilizes the EFR and confirmatory feature detectors processes described herein to analyze at least a portion of the CA signals to identify false AF detection. The false AF detections are used to generate or update a confirmation log 706. As described herein, the confirmation log 706 may include a log of the "false positive" episode counts from the original CA data set. The confirmation log 706 may also include corrective characterizations of individual events that were mischaracterized in the original CA data.

In certain instances, it may be desirable to return the confirmation log 706 information to the ICM as denoted at 703. In certain implementations, an ICM is provided with certain security features that prevent an external device (e.g., cell phone or local monitoring device) from directly changing sensitivity profile parameter settings and/or writing to any or at least certain sections of the memory within the ICM. For example, the security features may prevent an external device from writing over-sensitivity profile parameter settings and/or over the AF statistics and diagnostics that are generated and stored on the ICM.

Optionally, as a workaround, at 703, the confirmation log 706 may be written to a more flexible section of memory within the ICM (also referred to as an external device accessible section), along with header and/or metadata information tying the confirmation log 706 to a particular portion of the CA data. Additionally, or alternatively, at 704, the local external device may pass the confirmation log 706 to one or more remote devices and optionally to the database and server. The confirmation log 706 may be written to memory of an external device that interacts directly and regularly with the ICM, such as cell phone 614, local monitoring device 608, 616 and the like. The confirmation log 706 may be associated with particular CA data sets, such as based on time of data acquisition.

Optionally, a remote pairing session 708 may be performed between CA data on an ICM and locally externally stored confirmation logs. For example, the local external device may be directed to initiate a data transfer/download from the ICM, such as at 710, at a point in time separate from and after performing the AF detection confirmation processes described herein. The local external device receives the CA data set at 712 and determines, at 714, that the CA data set has already been analyzed to confirm AF detection. At 716, the local external device identifies a confirmation log stored at the local external device that corresponds to the CA data set, and at 716, appends the confirmation log to the associated CA data set, such as based on time of data acquisition. The cumulative information of the CA data set and confirmation log are transferred, through the external device, to a remote server 602, database 604, workstation 610, programmer 606 or otherwise.

By maintaining the confirmation log, for a particular CA data set at the local external device in association with the original CA data set, remote devices (e.g., programmer 606, server 602, etc.) receive and process both the original CA data set and the confirmation log. The remote device obtains the "traditional" device diagnostic sections, and is also afforded additional information from the confirmation log and is able to account (at 718) for cumulative adjustments/adjudications is AF detection before displaying a consolidated set of AF statistics and diagnostics to a physician or medical personnel.

Additionally, or alternatively, the operations of FIG. 7 may be implemented in connection with remotely stored confirmation logs, such as in communication sessions 720. At 722, a remote device may request CA data from a particular ICM by conveying a corresponding request to a local external device associated with the corresponding ICM. The local external device forwards the data request, at 724, to the ICM, in response thereto, at 726, the ICM transmits the CA data set to the local external device. The local external device forwards the CA data set, at 728, to the remote device. Optionally, before relaying the CA data set, at 728, the local external device may first determine whether the CA data set has first been analyzed for AF detection confirmation. In the example at 720, it is presumed that the CA data set has already been analyzed for AF detection confirmation and thus the local external device need not perform the confirmation analysis at this time. Additionally, or alternatively, the remote device may include, in the request, a direction to the local external device to not perform AF detection confirmation (e.g., the remote device knows that in AF detection confirmation has already been performed and stored elsewhere).

In connection with or separate from the request for CA data set at 722, the remote device conveys a request, at 730, to a server and database for any confirmation logs related to the requested CA data set. The requested may be broadcast to multiple external devices on the network or directed to a particular server/database known to maintain information in connection with the particular ICM. Additionally, or alternatively, the remote device may hold the request, at 730, until after receiving the CA data set, at 728. For example, once a remote device receives the CA data set, at 728, the remote device may include, within the request for confirmation logs, an indication of the time and date at which the CA data set was collected. In response to the request, the server and database return, at 732, one or more confirmation logs (if present). Thereafter, the remote device combines the CA data set and confirmation log to present a consolidated summary of the data to a physician or other medical personnel.

In connection with embodiments herein, the cloud-based approach allows an AF episode that is detected by the ICM using the traditional detection algorithms, to be passed through the local external device and stored at the server 602, database 604, workstation 610 or at another remote device within the cloud-based system. When an individual ICM is interrogated for a CA data set, the interrogation device would also request, from the cloud-based system, any additional information, such as any confirmation logs stored elsewhere within the system. For example, when an external device, such as a cell phone 614, local monitoring device 608, 616 and/or programmer 606 interrogate an individual ICM, the cell phone 614, local monitoring device 608, 616 and/or programmer 606 would also broadcast an ICM data supplement request over the cloud-based system. The ICM data supplement request requests additional data/information related to the individual ICM (e.g., based on the ICM serial number). In response thereto, the server 602 and/or other remote system may provide, to the requesting device, one or more confirmation logs or other information regarding past operation of the ICM. The requesting device then combines the CA data set from the ICM with related data (e.g., a confirmation log associated with a particular AF episode and/or group of cardiac events) from an external source. The external devices pulls data from the cloud in connection with ICM interrogation, and combine the CA data from the ICM with any corrective or confirmation data from the log, before presenting a consolidated data summary to a physician or medical personnel.

III. PVC DETECTION PROCESS

Figure 8:
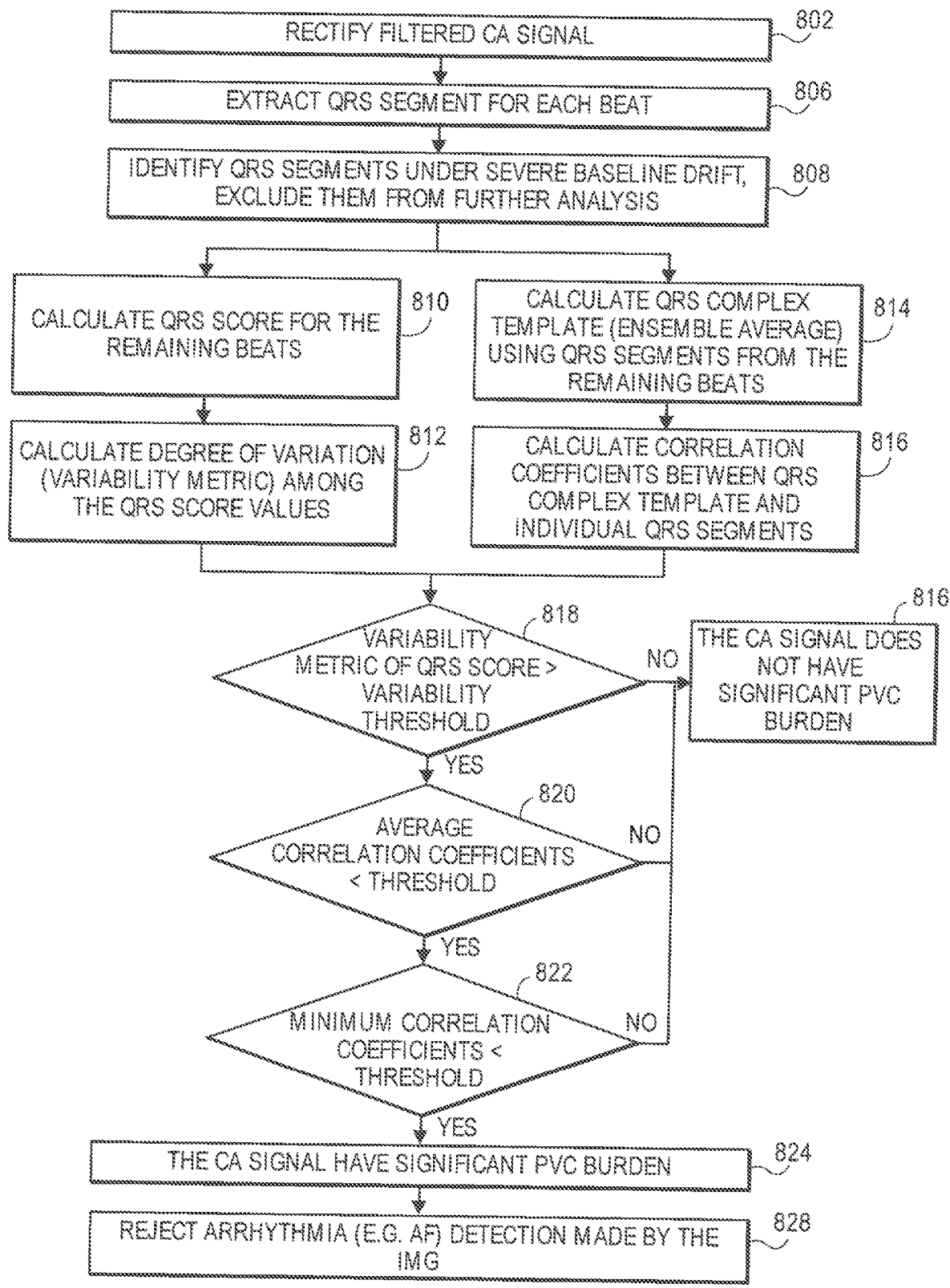
FIG. 8 illustrates a process for detecting a presence of premature ventricular contractions (PVCs) within cardiac activity signals in accordance with embodiments herein.

FIG. 8 illustrates a process for detecting a presence of premature ventricular contractions (PVCs) within cardiac activity signals in accordance with embodiments herein. In accordance with embodiments herein, the operations of FIG. 8 are implemented in real time by an IMD to process real-time cardiac activity signals in connection with detecting PVCs. The IMD may represent a ICM that is configured to analyze cardiac activity signals, declare arrhythmia episodes from the CA signals, and wireless transmit the CA data sets to an external device. Optionally, the IMD may represent a pacemaker, defibrillator, cardioverter, neurostimulator or other implantable device configured to delivery therapy. Additionally, or alternatively, the process of FIG. 8 may be implemented as part of a "second pass" or "confirmation process" to confirm a prior declaration of an AF episode by an IMD. When used in a confirmation process, the process of FIG. 8 operations upon a CA data set that was previously generated at the IMD to include CA signals and feature markers. The IMD analyzes the CA signals for a sinus feature, such as R-wave features. The CA signals are appended with a marker channel that includes features markers (e.g., sinus and/or arrhythmia markers such as R-wave markers, AF markers, etc. annotated by the implanted device). The feature markers are stored in connection with the CA signals to form a CA data set. The feature markers may be identified in connection with an arrhythmia detection process that is implemented by the ICM, by a local external device and/or by a remote server.

At 802, the one or more processors obtain and filter CA signals. By way of example, the processors may obtain the CA signals by at least one of i) accessing memory of an external device or remote server where the CA signals, information, etc. are stored, ii) receiving the CA signals over a wireless communications link between the IMD and a local external device, and/or iii) receiving the data CA signals at a remote server over a network connection. The obtaining operation, when from the perspective of an IMD, may include sensing new signals in real time, and/or accessing memory to read stored CA signals from memory within the IMD. The obtaining operation, when from the perspective of a local external device, includes receiving the CA signals at a transceiver of the local external device where the CA signals are transmitted from an IMD and/or a remote server. The obtaining operation may be from the perspective of a remote server, such as when receiving the CA signals at a network interface from a local external device and/or directly from an IMD. The remote server may also obtain the CA signals from local memory and/or from other memory, such as within a cloud storage environment and/or from the memory of a workstation or clinician external programmer.

By way of example, at 802, the one or more processors may apply a predetermined bandpass filter, such as a digital finite impulse response (FIR) bandpass filter, to filter the incoming CA signals. A shape of the bandpass filter may be defined by setting filter coefficients such that the filter suppresses low-frequency components (e.g., P waves and T waves) and suppresses high-frequency components (e.g., myopotential noise). The filter coefficients may be chosen to define a shape for the filter that preserves a morphology of intermediate frequency components, such as associated with a morphology of a PVC. At 802, the one or more processors rectify the filtered CA signal in order to convert all negative signal components to positive signal components for form rectified CA signals.

At 806, the one or more processors analyze a QRS complex for each beat or event within the rectified CA signals to identify a QRS feature of interest and a timing of the QRS feature of interest. For example, the QRS feature of interest and timing may correspond to as a peak of the QRS complex and a timing of the QRS complex peak ($T_{QRS\_PEAK}$).

At 808, the one or more processors identify QRS segments under severe baseline drift and exclude them from further analysis. For example, the processors may calculate, for each cardiac beat, an average signal level for the CA signal over the corresponding cardiac beat. For example, the processors may define a window that is centered over an individual beat, such as centered at the peak of the R wave. The window may have a predefined duration, such as 160 ms (e.g., 80 msec pre and 80 msec post QRS peak). The processors calculate the average for the QRS signal within the window and then step the averaging window to the next beat or QRS complex. The processors calculate the average at each beat by applying the averaging operation across the each QRS complex in the CA signals (e.g., across 840 beats over a 80 second EGM strip). The processors then determine whether to retain or reject an individual beat from further analysis by comparing the corresponding average to a drift threshold. The drift threshold may be defined in various manners, based upon the nature of the CA signal. For example, when the CA signal represents a voltage measurement that varies in millivolts in response to electrical potentials, the drift threshold may be defined as a millivolt threshold (e.g., 0.13 mV). The processors utilize the drift threshold to filter out QRS complex segments that exhibit a significantly high QRS average due to baseline drifting. For example, the CA signals will exhibit baseline drift when one or more electrodes utilized by the IMD experience separation from adjacent tissue (loss of contact) and/or fluid buildup at the tissue-electrode interface. Baseline drift may occur for other reasons as well and, if not corrected, will result in significant shifts in the amplitude of the QRS score $QRS_{SUM}$ for one or more beats.

Figure 9A:
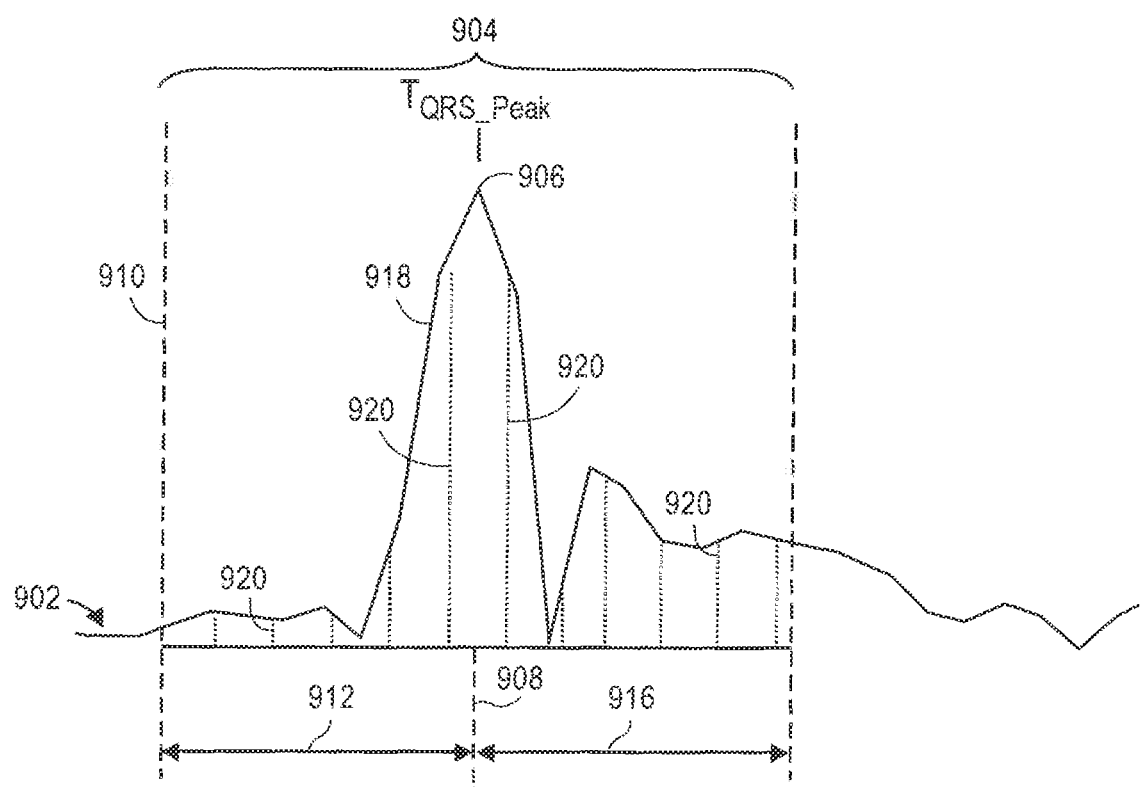
FIG. 9A illustrates a portion of a CA signal in connection with a single cardiac event or beat that is analyzed in connection with the process of FIG. 8.
Figure 9B:
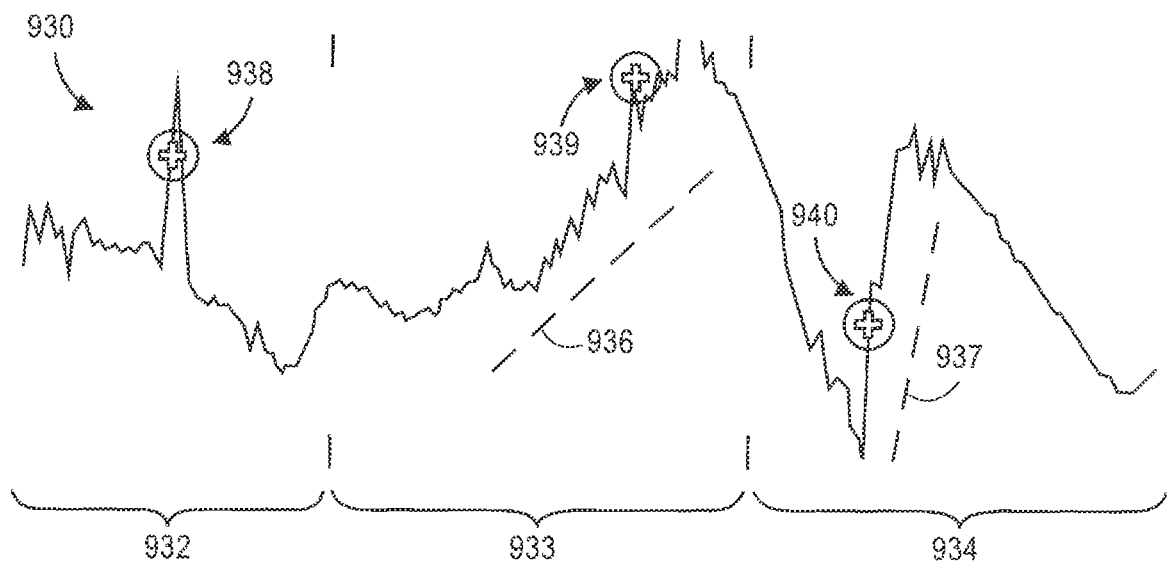
FIG. 9B illustrates a CA signal that includes a series of QRS complex segments having R-waves.

FIG. 9B illustrates a CA signal 930 that includes a series of QRS complex segments 932-934 having R-waves as noted at 938-940. The QRS complex segments 933 and 934 exhibit substantial baseline drift 936, 937, as noted by the dashed lines. The baseline drift 936, 937 causes the QRS complex segments 933, 934 to yield QRS scores ($QRS_{SUM}$) that are substantially larger than a normal QRS score associated with a normal QRS complex segment 932.

Returning to FIG. 8, at 808, the one or more processors reject the beats or cardiac events that have QRS complex segments that exhibit substantial baseline drift. For example, the one or more processors may perform baseline drift rejection, beat by beat, based on an average ($QRS_{AVG}$) exhibited across each corresponding QRS complex. For example, the average may be obtained by the processors utilizing a window of determined length (e.g., 160 ms window starting 80 ms before a QRS peak and continuing until 80 ms after the QRS peak). An average is calculated for each QRS complex and is compared by the processors to a drift threshold (e.g., $QRS_{AVG}>0.13$). When the average for an individual QRS complex segment exceeds the drift threshold, the processors determine that the corresponding beat exhibits sufficient (e.g., are corrupt) baseline drift to justify the processors removing/rejecting the QRS complex from further analysis. The operations at 810 remove baseline drift corrupted QRS complex segments, to form a drift corrected CA signal comprised solely of QRS complex segments that do not exhibit any baseline drift or exhibit a small amount of baseline drift insufficient to classify the corresponding beat as corrupt.

Additionally, or alternatively, the processors may apply a modified process to analyze QRS complex segments located at a beginning and an end of a CA signal strip (e.g., 1 second clip of EGM signals). The processors may exclude the QRS complex segments in the beginning and end portions of the CA signal strip.

Optionally, different threshold values may be utilized for baseline drift in order to modulate a sensitivity for signal drift detection. Optionally, the processors may apply a moving average that extends across adjacent QRS complex segments and compare the moving average to the drift threshold to determine whether to reject individual QRS complex segments.

At 810, the one or more processors calculate a QRS score ($QRS_{SUM}$) within a QRS complex segment for each of the remaining beat over of the CA signal. The QRS score is obtained, beat by beat, for each individual beat. The QRS score may be calculated for an individual beat by summing a series of amplitudes along the corresponding QRS complex segment. The processors sums amplitudes at evenly spaced sample points along the QRS complex segment to calculate the QRS score. Optionally, the summation of amplitudes may represent peak amplitude or peak slope within the window defined by the pre- and post-peak time durations. Additionally, or alternatively, the processors may calculate an energy of the QRS complex segment.

A location and length of the QRS complex segment is based on a timing of peaks in the QRS complex. For example, for each beat, a QRS complex segment is defined by a window that begins a pre-peak time duration before and ends a post—peak time duration after the peak of the QRS complex. A length of the pre- and post-peak time durations may be varied in connection with adjusting a sensitivity of the overall PVC detection process. When it is desirable to increase the PVC detection sensitivity, the overall length of the pre- and post-peak time durations may be increased. Alternatively, when it is desirable to decrease the PVC detection sensitivity, the overall length of the pre- and post-peak time durations may be decreased. By way of example only, each of the pre- and post-peak time durations may be set to between 80 and 80 ms, and as another example to approximately 50 ms.

FIG. 9A illustrates a portion of a CA signal 902 (e.g., an EGM strip) in connection with a single cardiac event or beat that is analyzed in connection with the process of FIG. 8. The CA signal 902 includes a QRS complex segment 904 that has a QRS complex peak 906 at a time 908. A QRS start time 910 precedes the QRS complex peak 906 ($T_{QRS\_Peak}$) by the pre-peak time duration 912 (Delta), while a QRS end time 914 follows the QRS complex peak 906 by the post-peak time duration 916 (Delta). At 808, the one or more processors calculate a QRS score (e.g., amplitude sums, energy, peak amplitude or peak slope) for the QRS complex 918. For example, a QRS score of the CA signal segment ($QRS_{SUM}$) from ($T_{QRS\_Peak}$− Delta) to ($T_{QRS\_Peak}$+ Delta) is obtained. By way of example, the processors may perform a summing operation over the QRS complex 918, whereby a sum is obtained for an amplitude of the QRS complex 918 at multiple discrete points along the QRS complex 918, as denoted by dashed lines 920. It is recognized that other techniques may be utilized to calculate the QRS score for the QRS complex 918, and that more or fewer discrete points may be included within the summation.

Returning to 810, the processors calculate the multiple QRS score values for multiple QRS complex segments of the CA signal over corresponding multiple cardiac cycles. For example, a 30 second segment of CA signals may include 340 beats or cardiac events and thus potentially a corresponding 340 QRS complex segments.

The processors calculate correlation coefficients between QRS morphologies of individual QRS complex segments and a QRS morphology template. For example, one or more standard morphologies may be defined as a QRS morphology template. The ensemble average of all QRS complex segments in the current CA signal can be used as a QRS morphology template. The processors compare the morphology of each QRS morphology segment to the QRS morphology template to derive a corresponding morphology correlation coefficient.

At 812, the one or more processors compute a variability metric for the QRS score (calculated at 810) from the drift corrected CA signal. For example, the processors may calculate the variability metric as a covariance of the QRS score. The covariance is based on the QRS complex segments that were not corrupted with baseline drift (e.g., did not exhibit a moving average that exceeded the drift threshold). The covariance $Cov\_QRS_{SUM}$ may represent a standard deviation of the QRS score $QRS_{SUM}$ for the QRS complex segments divided by the average of the QRS score $QRS_{SUM}$ for the QRS complex segments ($Cov\_QRS_{SUM}$=standard deviation (All $QRS_{SUM}$)/average (All $QRS_{SUM}$)).

The present example for the operations at 810-812 concern calculating QRS scores. Additionally, or alternatively, flow may move to 814, 816 where the one or more processors may compare morphologies of the QRS complex segments to one or more morphology templates. The comparison to the morphology templates provides morphology correlation coefficients that may be utilized as QRS scores for the corresponding QRS complex segments.

At 814, the one or more processors calculate a QRS complex template, namely a morphology ensemble from the QRS complex segments. For example, the morphology ensemble may represent an ensemble average of the QRS morphologies for all or a desired number of the drift corrected QRS complex segments.

At 816, the one or more processors compare each of the QRS morphologies against the QRS complex template (e.g., ensemble averaged QRS morphology). For example, the processors may determine and evaluate a correlation coefficient of each of the QRS morphologies against an ensemble averaged QRS morphology. The ensemble averaged QRS morphology is obtained using a subset of the QRS complex segments, namely the QRS complex segments that have a QRS score in a select range (e.g., an interquartile range such as the middle 50%).

At 818, the one or more processors determine whether the variability metric satisfies a first condition. For example, the first condition may represent a relatively high threshold for the covariance of the QRS complex segments. For example, the processors may determine whether the covariance $Cov\_QRS_{SUM}$ is greater than a PVC variability threshold ($Thresh_{PVC}$). By way of example, the PVC variability threshold may be 0.2, although other values may be utilized to modulate the sensitivity of the PVC detection. When the variability metric does not exceed the threshold, flow moves to 826. Otherwise, when the variability metric does exceed the threshold, flow moves to 820. The PVC variability threshold represents an extent to which the standard deviation and average for the QRS score may vary from one another while still representing sinus behavior, or at least a level of PVC burden that is below a burden threshold. Accordingly, at 826, the processors declare the CA signals to have little or non-significant PVC burden and the process of FIG. 8 ends.

At 820, the one or more processors determine whether the average correlation coefficient is less than a predetermined threshold (e.g., 0.92). When the average correlation coefficient is below the threshold, flow moves to 822. Alternatively, when the average correlation coefficient exceeds the threshold, flow advances to 826. At 820, the processors analyze correlation characteristics based on comparisons of QRS morphologies to QRS morphology templates. At 826, the processors declare the CA signals to have little or non-significant PVC burden and the process of FIG. 8 ends.

At 822, the one or more processors determine whether all or a predetermined number of the QRS complex segments have a minimum correlation coefficient that is below a minimum threshold. For example, the processors may determine whether all of the QRS complex segments have a minimum correlation coefficient of less than 0.75. When the QRS complex segments have a minimum correlation coefficient that is less than the minimum threshold, flow advances to 826, where the processors declare that the CA signals exhibit nonsignificant PVC burden. When flow advances to 826, the processors determine that, to the extent PVC burden exist, the presence of PVCs non-insignificant. A nonsignificant level of PVCs may be present, such as when R wave morphologies are significantly consistent with each other and the morphology variance is likely due to amplitude changes. Different thresholds may be utilized in connection with analyzing average and minimum correlation coefficients in order to modulate the sensitivity.

Alternatively, when the processors determine at 822 that the QRS complex segments have a minimum correlation coefficient that equals or is greater than the minimum threshold, flow advances to 824. At 824, the one or more processors declare that the CA signals exhibit significant PVC burden.

At 828, the one or more processors reject a prior device documented arrhythmia (e.g., AF) that was declared by the ORI process of the ICM or IMD. For example, with reference to the operations of FIG. 3, at 828, when the CA signals are declared to have significant PVC burden, the one or more processors may reject the original detection of AF episode. Additionally, or alternatively, the one or more processors may exclude any beats that that are identified as PVC beats and reevaluate the CA signals for AF while excluding the identified PVC beats. The operations at 820 and 822 avow the processors to analyze consistency within the QRS complex signals. If QRS complex segments are not consistent, in accordance with the thresholds at 820, 822, the processors declare a presence of PVCs in the cardiac signal.

Additionally, or alternatively, in detecting AF, R-R interval stability may need to be re-evaluated excluding those QRS complexes detected as PVCs because significant R-R interval instability may still be caused by non-PVC QRS complexes. For instance, if the covariance of RR intervals is <0.12 excluding PVCs, the original AF diagnostic may be reversed. Alternatively, if $Cov\_QRS_{SUM}$ is very high (e.g., greater than $2 \times Thresh_{PVC}$), the original AF diagnostic may be reversed without analyzing the covariance of RR intervals.

Figure 9C:
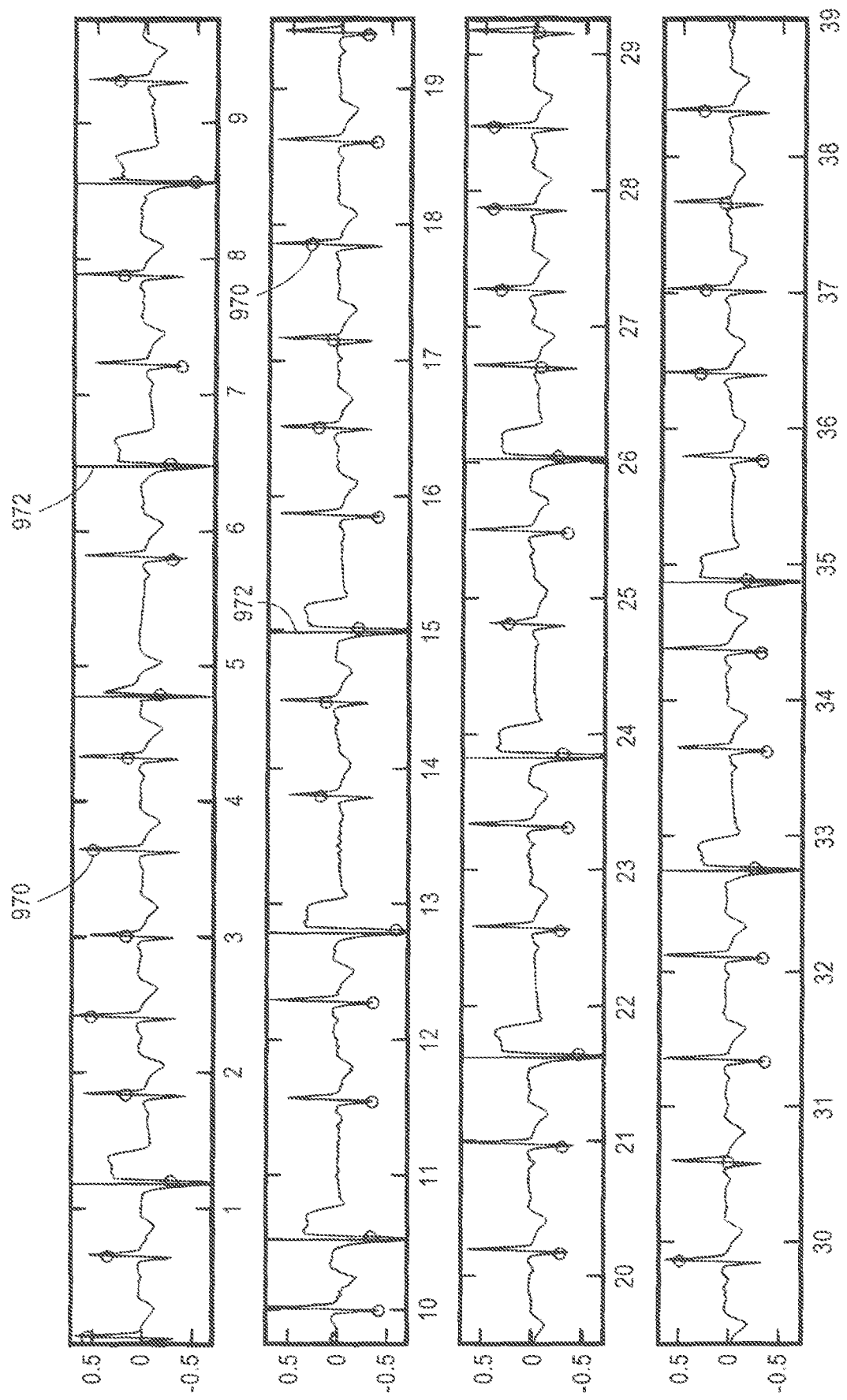
FIG. 9C illustrates multiple panels of a CA signal strip analyzed in accordance with embodiments herein.

FIG. 9C illustrates multiple panels of a CA signal strip (e.g., EGM signals over a 39 second interval) analyzed in accordance with embodiments herein. In the CA signal strip, a portion of the QRS complex segments have been rejected as exhibiting excessive PVC burden in accordance with the operations of FIG. 8. The circles 970 indicate device documented R waves, wherein the IMD has determined that an R-wave is present in the CA signals. As explained herein, when excessive PVCs occur, the IMD may identify false positives, namely features of the CA signals to represent R-waves when an R-wave is in fact not present. The vertical ones 972 indicate PVCs detected by the process of FIG. 8. When the IMD declares false R-waves, the IMD will also determine an RR interval that is not necessarily representative of the patient's cardiac activity. The false R-waves may lead the IMD to identify irregularities in the RR interval which in turn leads the IMD to declare a false AF episode. For example, a false AF episode may be declared due to R-R interval instability introduced by PVCs as PVCs tend to introduce a short RR interval followed by long RR interval.

The operation at and after 816 may vary based on whether the process of FIG. 8 is implemented as a first pass detection algorithm or a second/confirmation pass detection algorithm. As a first pass detection algorithm, the process of FIG. 8 analyzes CA signals for a first time without prior analysis by an IMD or otherwise. For example, the PVC detection process of FIG. 8 may be implemented by an IMD as a part of, or in parallel with, an arrhythmia detection algorithm. The IMD may apply the PVC detection first and then apply the arrhythmia detection algorithm.

Alternatively, as a second/confirmation detection algorithm, the process of FIG. 8 analyzes CA signals that have already been analyzed by the IMD and labeled with event markers. During a second/confirmation detection process, at 816, the one or more processors may confirm a prior determine by the IMD (e.g., confirm arrhythmia, confirm sinus behavior).

Closing

The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C # or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and physical characteristics described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A computer implemented method for detecting premature ventricular contractions (PVCs) in cardiac activity, comprising:
    under control of one or more processors configured with specific executable instructions,
    obtaining cardiac activity (CA) signals for a series of beats;
    for at least a portion of the series of beats, calculating QRS scores for corresponding QRS complex segments from the CA signals;
    calculating a variability metric for QRS scores across the series of beats;
    calculating a QRS complex template using QRS segments from the series of beats;
    calculating correlation coefficients between the QRS complex template and the QRS complex segments,
    comparing the variability metric to a variability threshold and the correlation coefficients to a correlation threshold, and
    designating the CA signals to include a predetermined level of PVC burden based on the comparing.

2. The method of claim 1, wherein the calculating the QRS scores comprises calculating at least one of a summation, area under a curve, or energy for the QRS complex segments.

3. The method of claim 1, further comprising: creating a morphology ensemble from the QRS complex segments; and comparing the morphology ensemble to QRS morphologies for the corresponding QRS complex segments to obtain morphology correlation characteristics for the QRS complex segments.

4. The method of claim 1, wherein the computing of the variability metric includes calculating a covariance Cov_QRS from the QRS scores, the covariance based on the QRS scores.

5. The method of claim 4, wherein the covariance Cov_QRS represents a standard deviation of the QRS scores of the QRS complex segments divided by an average of the QRS scores, the QRS scores representing at least one of amplitude sums, energy or area under the curve for the corresponding QRS complex segments.

6. The method of claim 1, wherein, when the variability metric does not satisfy the variability threshold, declaring the CA signals to include an non-significant PVC burden which is less than the predetermined level of PVC burden.

7. The method of claim 1, wherein the morphology ensemble represents an ensemble average of the QRS morphologies for a desired number of the QRS complex segments; and the comparing includes comparing the QRS morphologies for the corresponding QRS complex segments to the ensemble average to obtain the morphology correlation characteristics.

8. The method of claim 7, wherein the morphology correlation characteristics represent correlations between the ensemble average and the QRS morphologies of each of the QRS complex segments.

9. The method of claim 1, further comprising rejecting the beats from the CA signals that exhibit a predetermined level of baseline drift.

10. The method of claim 1, when the variability metric satisfies the variability threshold and the correlation coefficients satisfies the correlation conditions, declaring the CA signals to have significant PVC burden.

11. A system for detecting premature ventricular contractions (PVCs) in cardiac activity, comprising:
    memory to store executable instructions;
    one or more processors that, when executing the executable instructions, configured to:
        obtain a cardiac activity (CA) signals for a series of beats;
        for at least a portion of the series of beats, calculate QRS scores for corresponding QRS complex segments from the CA signals;
        calculate a variability metric for QRS scores across the series of beats;
        calculate a QRS complex template using the QRS complex segments;
        calculate correlation coefficients between the QRS complex template and the QRS complex segment;
        comparing the variability metric to a variability threshold and the correlation coefficients to a correlation threshold, and
        designating the CA signals to include a predetermined level of PVC burden based on the comparing.

12. The system of claim 11, wherein the one or more processors are configured to calculate the QRS scores comprises calculating at least one of a summation, area under a curve, or energy for the QRS complex segments.

13. The system of claim 11, wherein the one or more processors are configured to create a morphology ensemble from the QRS complex segments; and compare the morphology ensemble to QRS morphologies for the corresponding QRS complex segments to obtain morphology correlation characteristics for the QRS complex segments, the designation based on the morphology correlation characteristics.

14. The system of claim 13, wherein the morphology correlation characteristic represents an average correlation coefficient, and wherein the determining includes determining whether the average correlation coefficient is smaller than the predetermined threshold.

15. The system of claim 13, wherein the morphology correlation characteristic represents a minimum correlation coefficient, and wherein the determining includes determining whether the minimum correlation coefficient for the QRS complex segments is smaller than a minimum threshold.

16. The system of claim 13, wherein the morphology ensemble represents an ensemble average of the QRS morphologies for a desired number of the QRS complex segments; and the comparing includes comparing the QRS morphologies for the corresponding QRS complex segments to the ensemble average to obtain the morphology correlation characteristics.

17. The system of claim 11, wherein the one or more processors are configured to compute the variability metric by calculating a covariance $Cov\_QRS_{SUM}$ from the QRS scores, the covariance based on the QRS complex segments.

18. The system of claim 11, wherein, when the variability metric does not satisfy the variability threshold, declaring the CA signals to include non-significant PVC burden which is less than the predetermined level of PVC burden.

19. The system of claim 1, wherein, when the correlation coefficients do not satisfy the correlation threshold, declaring the CA signals do not have significant PVC burden.

20. The system of claim 1, wherein, when the variability metric satisfied the variability threshold and the correlation coefficients satisfy the correlation threshold, declaring the CA signals to have significant PVC burden.

21. The system of claim 20, wherein, when declaring the CA signals to have significant PVC burden, rejecting an original detection of AF episode, or reevaluating if the CA signals include AF by excluding identified PVC beats.

* * * * *